(12) United States Patent
Colliou et al.

(10) Patent No.: US 7,020,531 B1
(45) Date of Patent: Mar. 28, 2006

(54) GASTRIC DEVICE AND SUCTION ASSISTED METHOD FOR IMPLANTING A DEVICE ON A STOMACH WALL

(75) Inventors: Olivier Colliou, Los Gatos, CA (US); Kevin Nason, Menlo Park, CA (US); Harm TenHoff, Mountain View, CA (US); Mir A. Imran, Los Altos Hills, CA (US); Ted Layman, Park City, UT (US)

(73) Assignee: Intrapace, Inc., Menlo Park, CA (US)

( * ) Notice: Subject to any disclaimer, the term of this patent is extended or adjusted under 35 U.S.C. 154(b) by 80 days.

(21) Appl. No.: 10/116,481

(22) Filed: Apr. 2, 2002

Related U.S. Application Data

(63) Continuation-in-part of application No. 09/847,884, filed on May 1, 2001, now Pat. No. 6,535,764.

(60) Provisional application No. 60/337,194, filed on Dec. 6, 2001.

(51) Int. Cl.
*A61N 1/05* (2006.01)
*A61K 9/22* (2006.01)

(52) U.S. Cl. .................................... 607/133; 604/891.1
(58) Field of Classification Search ................. 607/40, 607/133, 116, 137; 600/377; 604/891.1
See application file for complete search history.

(56) References Cited

U.S. PATENT DOCUMENTS

| | | | |
|---|---|---|---|
| 3,411,507 A | 11/1968 | Wingrove | 128/422 |
| 3,646,940 A | 3/1972 | Timm et al. | 128/421 |
| 3,662,758 A | 5/1972 | Glover | 128/419 |
| 3,796,221 A | 3/1974 | Hagfors | 128/421 |

(Continued)

FOREIGN PATENT DOCUMENTS

| | | | |
|---|---|---|---|
| EP | 0129483 | 12/1984 | 1/36 |
| EP | 0442588 | 8/1991 | 17/68 |
| EP | 0571938 | 4/1999 | 1/36 |
| US | 3815611 | 6/1974 | 128/419 |
| WO | 9853878 | 12/1998 | 1/5 |
| WO | 0158389 | 8/2001 | 2/48 |
| WO | 0176690 | 10/2001 | 1/18 |

OTHER PUBLICATIONS

U.S. Patent Application Publication 2002/0103424 to Swoyer et al. Pub Date Aug. 1, 2002., provisional application 60/265513 filed Jan. 31, 2001.*

H. Geldof, et al., Electrogastrographic Study of Gastric Myoelectrical Activity In Patients With Unexplained Nausea And Vomiting, *Gut,* 27:799–808, (1986).

(Continued)

*Primary Examiner*—Jeffrey R. Jastrzab
(74) *Attorney, Agent, or Firm*—Susan M. Schmitt; Peters, Verny, Jones, Schmitt & Aston LLP

(57) ABSTRACT

A device, system and method for diagnosing and treating a patient is provided where a functional device is attached to a stomach wall. The device in one embodiment provides electrical stimulation of the stomach wall. The device may also have other functional aspects such as a sensor for sensing various parameters of the stomach or stomach environment, or a substance delivery device. The implant may be programmed to respond to sensed information or signals. The device may be modular with a portion of the device accessible for removal and replacement. In one embodiment, an endoscopic delivery system delivers the functional device through the esophagus and into the stomach where it is attached the stomach wall with the assistance of a suction used to stabilize the tissue of the stomach wall. The device includes a chamber for receiving tissue of the stomach wall for attachment where a vacuum pressure is applied through the chamber to draw the tissue into the chamber.

6 Claims, 27 Drawing Sheets

U.S. PATENT DOCUMENTS

| | | | |
|---|---|---|---|
| 4,102,344 A | 7/1978 | Conway et al. | 128/419 |
| RE30,366 E | 8/1980 | Rasor et al. | 128/419 |
| 4,628,928 A | 12/1986 | Lowell | 128/303 |
| 4,823,808 A | 4/1989 | Clegg et al. | 128/773 |
| 4,925,446 A | 5/1990 | Garay et al. | 604/96 |
| 5,188,104 A | 2/1993 | Wernicke et al. | 128/419 |
| 5,292,344 A * | 3/1994 | Douglas | 607/40 |
| 5,415,181 A | 5/1995 | Hogrefe et al. | 128/736 |
| 5,423,872 A | 6/1995 | Cigaina | 607/40 |
| 5,540,730 A | 7/1996 | Terry, Jr. et al. | 607/40 |
| 5,558,640 A | 9/1996 | Pfeiler et al. | 604/67 |
| 5,690,691 A | 11/1997 | Chen et al. | 607/40 |
| 5,836,994 A | 11/1998 | Bourgeois | 607/40 |
| 5,861,014 A | 1/1999 | Familoni | 607/40 |
| 5,928,195 A | 7/1999 | Malamud et al. | 604/141 |
| 5,993,473 A | 11/1999 | Chan et al. | 606/192 |
| 5,995,872 A | 11/1999 | Bourgeois | 607/40 |
| 6,026,326 A | 2/2000 | Bardy | 607/40 |
| 6,041,258 A | 3/2000 | Cigaina et al. | 607/40 |
| 6,083,249 A | 7/2000 | Familoni | 607/40 |
| 6,091,992 A | 7/2000 | Bourgeois et al. | 607/40 |
| 6,097,984 A | 8/2000 | Douglas | 607/40 |
| 6,104,955 A | 8/2000 | Bourgeois | 607/40 |
| 6,115,635 A | 9/2000 | Bourgeois | 607/40 |
| 6,216,039 B1 | 4/2001 | Bourgeois | 607/40 |
| 6,243,607 B1 | 6/2001 | Mintchev et al. | 607/40 |
| 6,321,124 B1 | 11/2001 | Cigaina | 607/133 |
| 6,327,503 B1 | 12/2001 | Familoni | 607/40 |
| 6,381,495 B1 | 4/2002 | Jenkins | 607/40 |
| 6,449,511 B1 | 9/2002 | Mintchev et al. | 607/40 |
| 6,453,199 B1 | 9/2002 | Kobozev | 607/40 |
| 6,477,423 B1 | 11/2002 | Jenkins | 607/40 |
| 6,510,332 B1 | 1/2003 | Greenstein | 600/377 |
| 6,529,778 B1 * | 3/2003 | Prutchi | 607/119 |
| 6,540,789 B1 | 4/2003 | Silverman et al. | 623/23.65 |
| 6,542,776 B1 | 4/2003 | Gordon et al. | 607/40 |
| 6,564,101 B1 | 5/2003 | Zikria | 607/40 |
| 6,600,953 B1 | 7/2003 | Flesler et al. | 607/40 |
| 6,606,523 B1 | 8/2003 | Jenkins | 607/133 |
| 6,611,715 B1 | 8/2003 | Boveja | 607/40 |
| 6,615,084 B1 | 9/2003 | Cigaina | 607/40 |
| 2002/0103424 A1 | 8/2002 | Swoyer et al. | 600/350 |
| 2002/0103521 A1 | 8/2002 | Swoyer et al. | 607/116 |
| 2002/0103522 A1 | 8/2002 | Swoyer et al. | 607/116 |

OTHER PUBLICATIONS

Brent W. Miedema, et al., Pacing The Human Stomach, *Surgery*, 143–150, (Feb. 1992).

Keith A. Kelly, Differential Responses Of The Canine Gastric Corpus And Antrum To Electric Stimulation, *Am. J. of Physiology*, 226/1:230–234, (Jan. 1974).

Electric Stimulation of the Gastrointestinal Tract, GP, p. 151 (Apr. 1964).

Michael P. Hocking, Postoperative Gastroparesis And Techygastria–Response to Electric Stimulation and Erythromycin, *Surgery*, 114/3:538–542 (Sep. 1993).

Keith A. Kelly et al., Role of the Gastric Pacesetter Potential Defined by Electrical Packing, *Canadian J. of Physiology and Pharmacology*, 50:1017–1019, (1972).

Babajide O. Familoni, Efficacy of Electrical Stimulation at Frequencies Higher Than Basal Rate in Canine Stomach, *Digestive Diseases and Sciences*, 42/5:892–897, (May 1997).

Bader–Eddine Bellahsene, et al., Evaluation of a Portable Gastric Stimulator, Ninth Annual Conference of the Engineering in Medicine and Biology Society, (1987).

J. Chris Eagon, et al., Effects of Gastric Pacing on Canine Gastric Motility and Emptying, *The American Physiological Society*, 265/4:G767–G774, (Oct. 1993).

Babajide O. Familoni, et al., Electrical Pacing of the Stomach in Dogs,.

S. K. Sarna, et al., Electrical Stimulation of Gastric Electrical Control Activity, *Am. J. of Physiology*, 225/1:125–131, (Jul. 1973).

S. K. Sarna, et al., Gastric Pacemakers, *Gastroenterology*, 70:226–231, (1976).

Edwin E. Daniel, et al., Electrical Activity of the Gastrointestinal Tract as an Indication of Mechanical Activity, *Am. J. of Digestive Diseases*, 8/1:54–102, (1963).

M. Kubota, et al., Manometric Evaluation of Children With Chronic Constipation Using a Suction–Stimulating Electrode, *Eur. J. Pediatr. Surg.*, 2:287–290, (1992).

Chul H. You, et al., Electrogastrographic Stud of Patients With Unexplained Nausea, Bloating, and Vomiting, *Gastroenterology*, 79:311–314 (1980).

Cigaina, et al., Gastric Myo–Electrical Pacing As Therapy for Morbid Obesity: Preliminary Results.

Kelly, et al., Pacing the Canine Stomach With Electric Stimulation, *Am. J. of Physiology*, 222/3:588–594, (Mar. 1972).

Eagon, et al., Gastrointestinal Pacing, *Gastrointestinal Tract*, 73/6:1161–1172, (Dec. 1993).

Swain, et al., An Endoscopically Deliverable Tissue–Transfixing Device For Securing Biosensors in the Gastrointestinal Tract, *Gastrointestinal* Endoscopy/6:730–734, (1994).

* cited by examiner

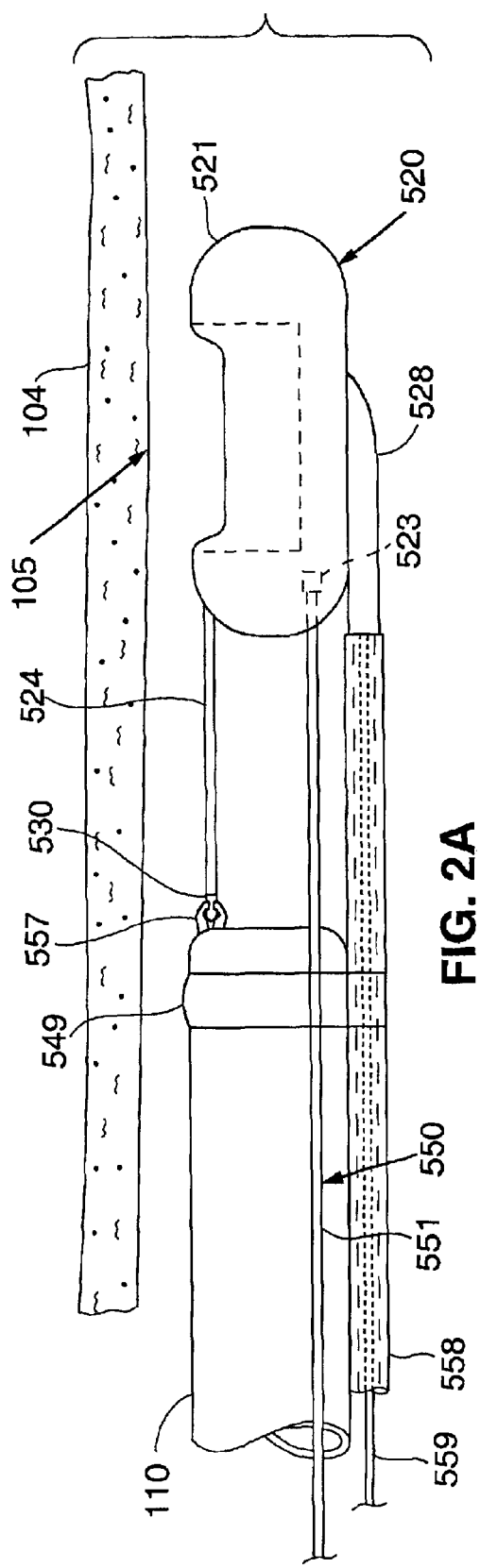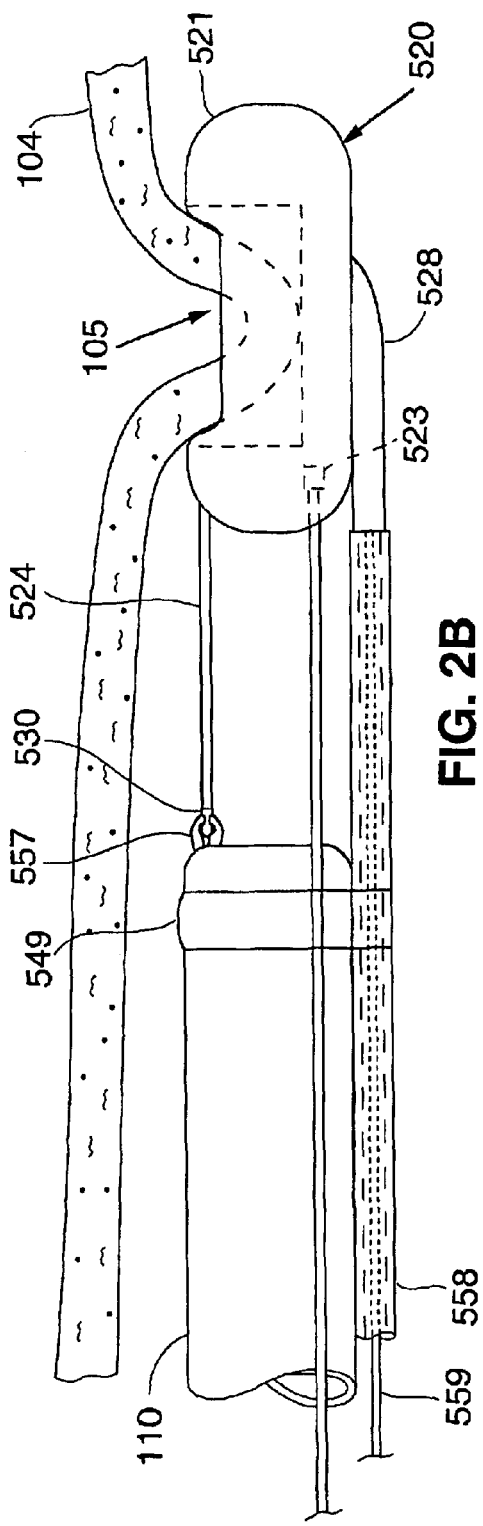
FIG. 2A
FIG. 2B

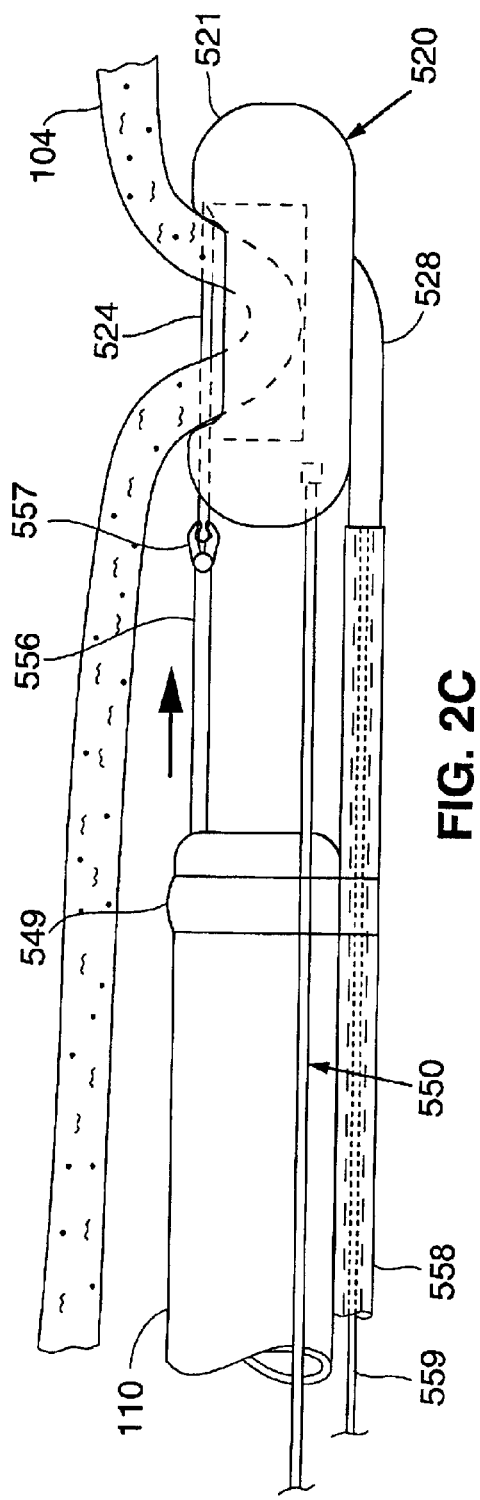
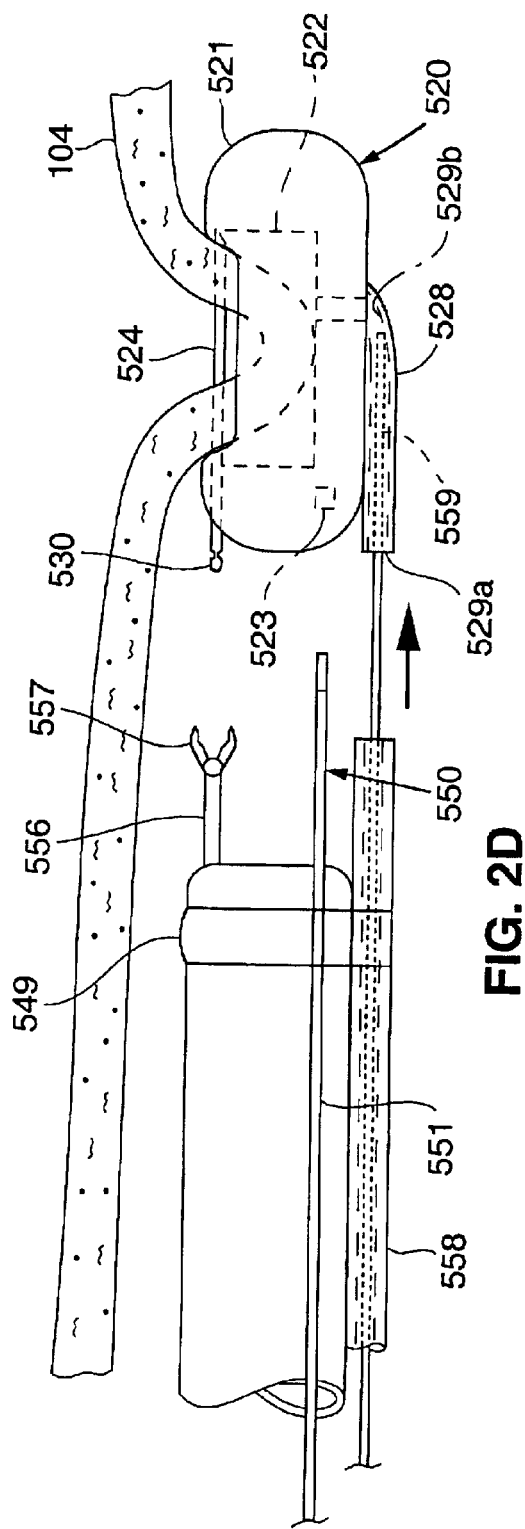
FIG. 2C
FIG. 2D

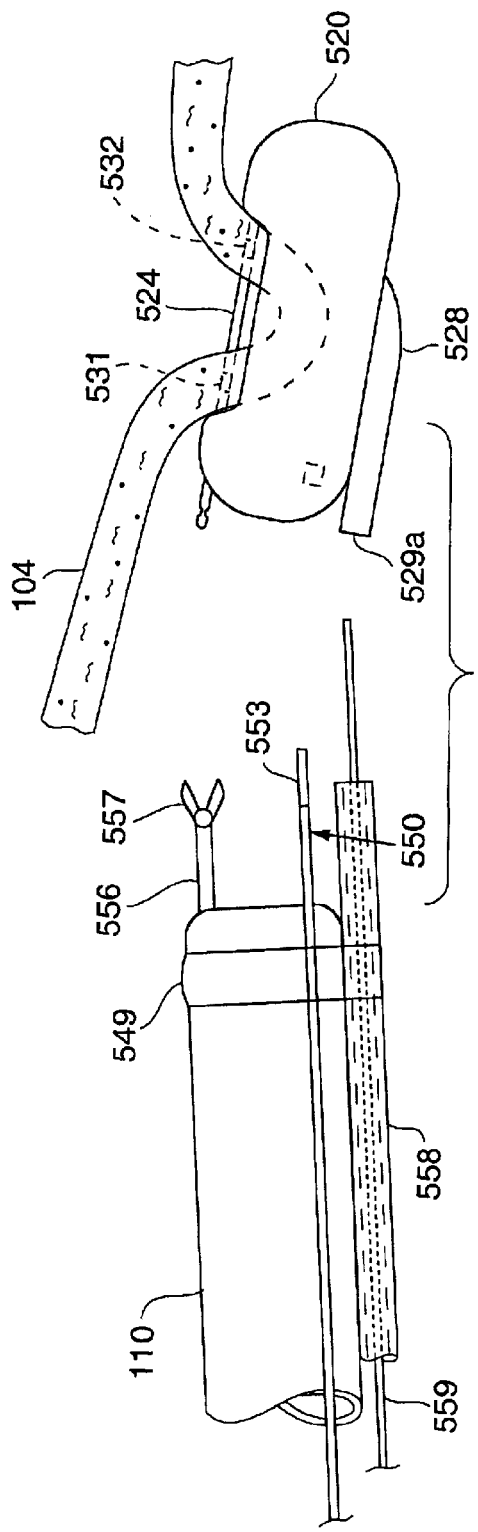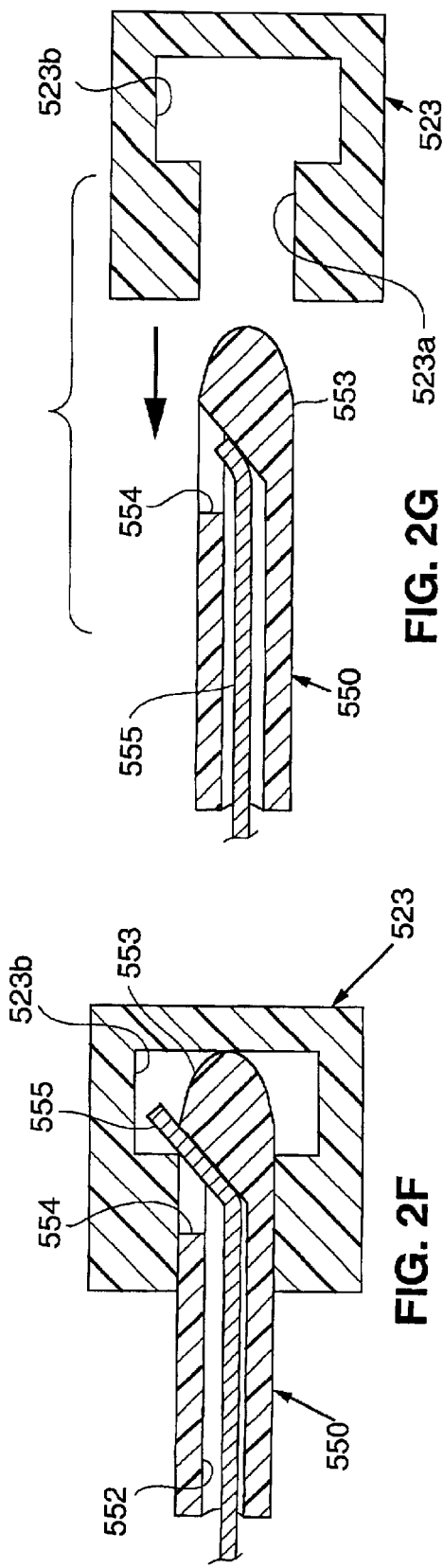

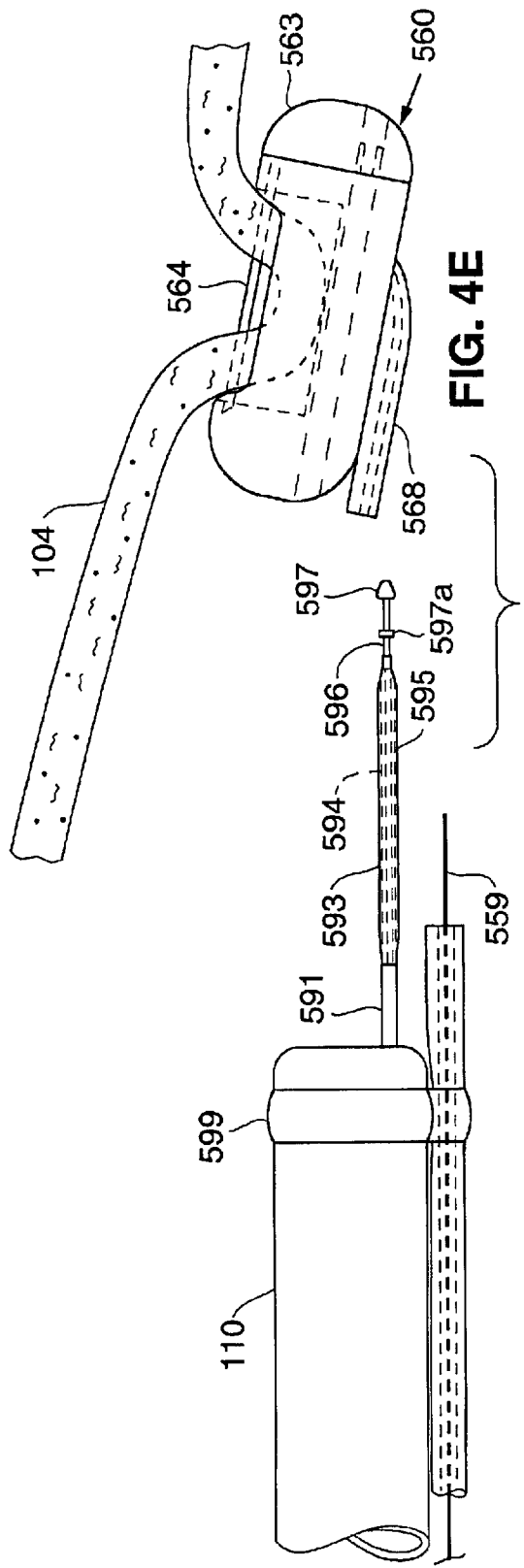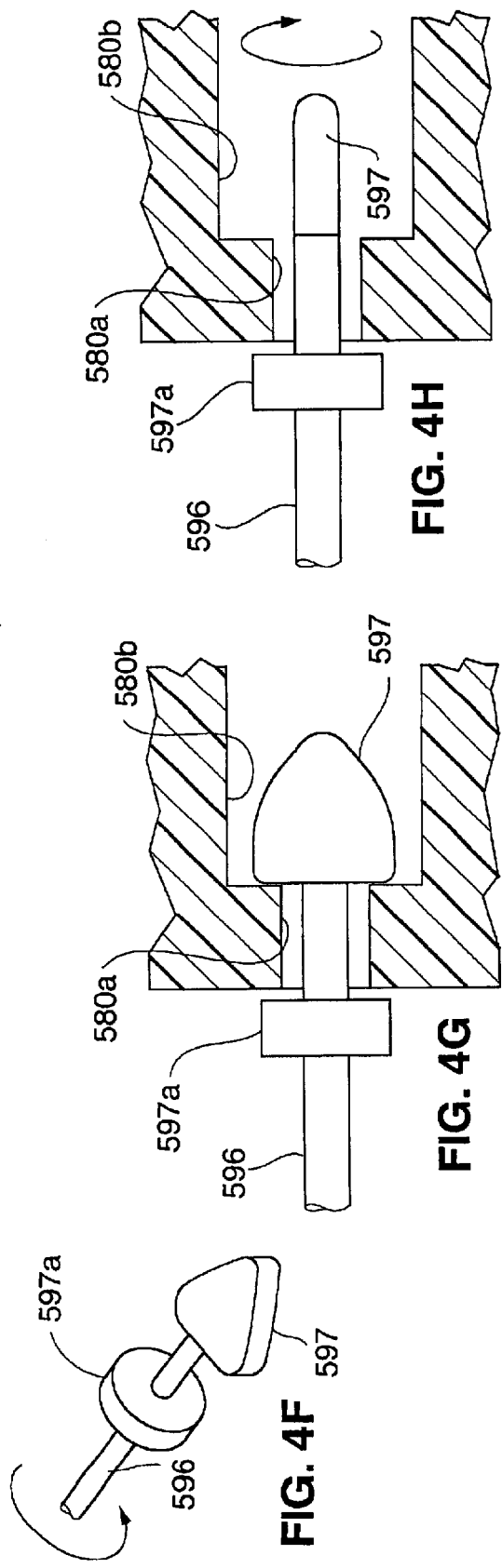

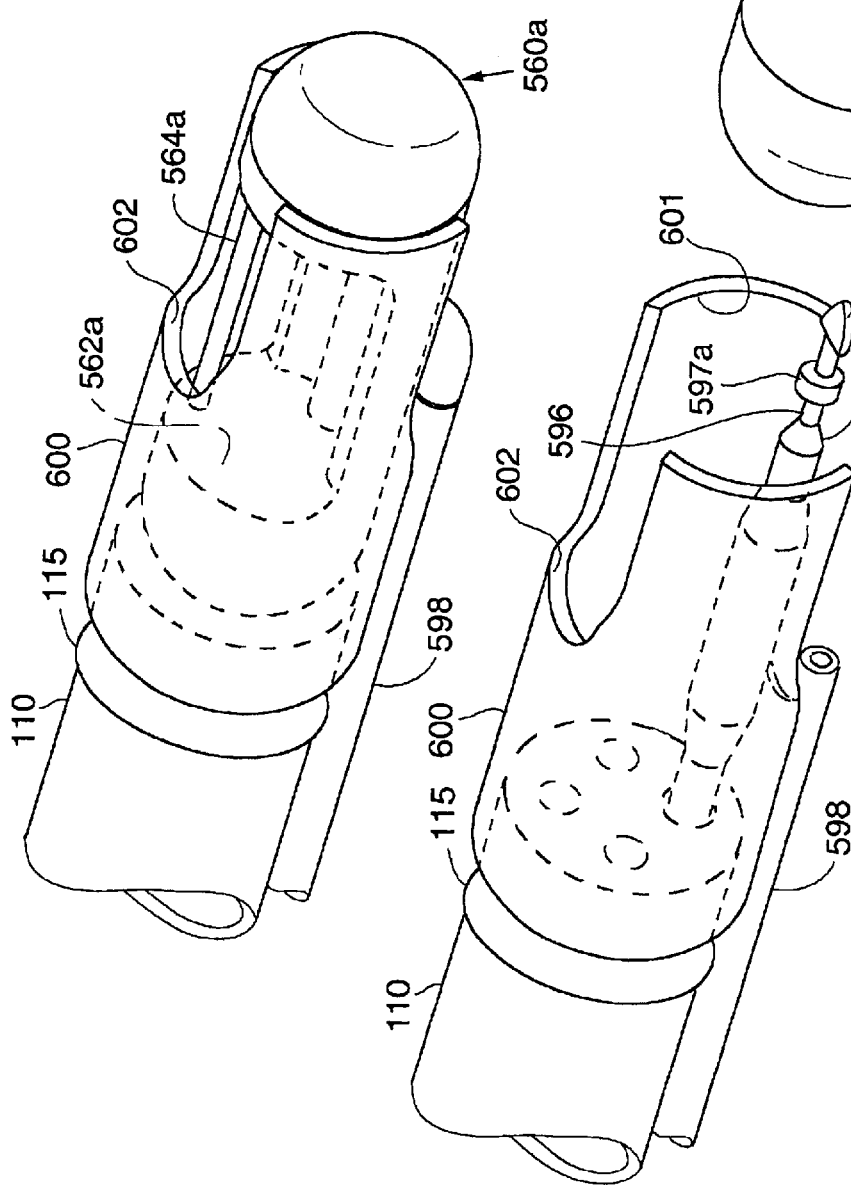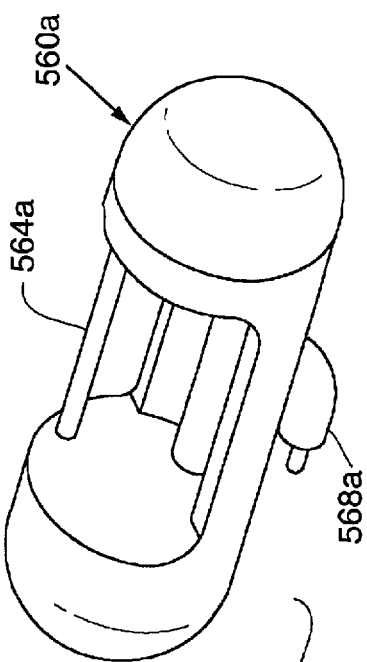
FIG. 5A
FIG. 5B

GASTRIC DEVICE AND SUCTION ASSISTED METHOD FOR IMPLANTING A DEVICE ON A STOMACH WALL

This application is a continuation in part of U.S. application Ser. No. 09/847,884 entitled GASTRIC TREATMENT DIAGNOSIS DEVICE AND METHOD, filed on May 1, 2001 now U.S. Pat. No. 6,535,764 and claims priority of Provisional Application Ser. No. 60/337,194 filed Dec. 6, 2001.

FIELD OF THE INVENTION

This invention relates to an implantable device for treating or diagnosing stomach conditions. One aspect of the invention relates to implanting a functional device using suction assisted methods and devices. One embodiment of the invention relates to a system and a method for electrically stimulating the stomach wall to effect gastric motility or otherwise treat gastrointestinal related disorders.

BACKGROUND OF THE INVENTION

Various organs of the gastrointestinal tract such as the stomach, small intestine and colon contain cells that are believed to govern the organs' periodic contractile behavior. In healthy humans, in certain regions of the organs, these cells generate and propagate rhythmic electrical signals. In general, several types of electrical potential activities have been observed in the gastrointestinal tract. Consistent slow wave or pacesetter potentials have been observed and higher frequency spike activity has been observed. The pacesetter potentials are continuously propagating, relatively low frequency, cyclic depolarizations of the smooth muscle cell lining. The higher frequency spike bursts generally correspond with smooth muscle contractile activity and peristalsis. In general, when the spike burst activity occurs, it appears to be at a fixed time delay with respect to the slow wave potentials. It is believed that when the pacesetter potentials are combined with a chemical or neural excitation of the cells, smooth muscle contractile activity occurs. Also it is believed that the pacesetter potentials control and coordinate the frequency and direction of the contractions.

Electrical stimulation of the gastrointestinal tract has been proposed to treat motility related disorders and other gastrointestinal diseases or conditions. The electrical stimulation has been proposed in a number of forms, such as, e.g., pacing, electrical contractile stimulation or other stimulation, e.g., to treat nausea or obesity. Electrical pacing of the gastrointestinal tract is generally defined as a periodic electrical stimulation that captures and/or controls the frequency of the pacesetter potential or slow wave activity of the gastrointestinal organ (including in a retrograde direction). Electrical contractile stimulation generally refers to stimulation that directly causes or results in muscular contraction associated with the gastrointestinal tract. In some disease states, dysrhythmias of the gastric pacesetter potentials may be present. The result of the abnormal pacesetter potentials may be gastric retention of food. Electrical stimulation of gastric tissue has been proposed to induce peristalsis. Electrical stimulation has also been proposed to treat obesity by altering gastric motility, or by stimulating neural pathways. For example, one treatment method causes the stomach to retain food for a greater duration. Electrical stimulation has also been proposed to slow the gastric emptying to treat a disorder known as dumping syndrome where the stomach empties at an abnormally high rate into the small intestine causing various gastrointestinal disorders. In particular, electrical pacing of gastric pacesetter potentials has been proposed to induce regular rhythms for the pacesetter potentials with the intent of inducing regular or controlled gastric contractions.

Within the stomach, at least one pacemaker region has been identified near the interface of the fundus and the corpus along the greater curvature. This region has been one target for gastric pacing. Peristalsis controlled by this region is believed to serve to mix and break down food and propel small particles through the pylorus into the duodenum. It is believed that gastric emptying of liquids is controlled by the fundus. This region is believed to create with characteristic contractions, a pressure gradient between the fundus, pylorus and duodenum that relates to the rate of gastric emptying.

An early attempt at a gastric stimulation device included an electrode at the end of a nasogastric tube or catheter. The nasogastric tube was passed into the stomach transnasally. Electrical stimulation was applied through the electrode on the end of the tube using an external stimulator unit. The return electrode was placed on the abdomen. This device required a transnasal procedure whenever stimulation was required. It would therefore be desirable to provide a device that could reside in the stomach for a long-term treatment protocol.

Other devices used to pace the stomach have generally been implanted by accessing the outside of the stomach through an opening in the abdomen, either through open surgery or laparoscopic surgery. Electrodes have been attached to the stomach wall with attached leads extending through the abdomen.

These procedures involve implanting a pacemaker device in a subcutaneous or sub-muscular pocket. The devices are anchored into the subcutaneous or sub-muscular pocket initially by a suture anchor and eventually by fibrous tissue ingrowth around the unit. The pacemaker device housing is typically constructed of a titanium or stainless steel material with connectors molded into an epoxy header. The devices are thin in one dimension so that they are less visible when implanted directly under the skin or muscle layer. Therefore, in order to accommodate the necessary battery capacity, the devices are widely shaped, e.g. round or kidney shaped in the other two dimensions. The leads extend from the unit's epoxy header to a stimulation site remote from the pacemaker unit.

A gastrointestinal pacemaker having phased multi-point stimulation has been proposed with electrodes placed in multiple points around the GI tract including on the inner or outer surface of the stomach. As described, the device could be preprogrammed or include an implantable pacemaker detachably coupled to the multiple electrodes in their various locations, and including an electronic controller that may be programmed by using an external programmer to set stimulation parameters. The implantable pacemaker is located remote from the stimulation sites.

Some gastric stimulation procedures have proposed electrical stimulation in response to sensing electrical pulses within the stomach within a particular range. Additionally, a device has been proposed to sense electrical parameters to determine the fullness of an organ and the absence of muscular contraction, and to deliver electrical muscular contraction stimulation to the organ in response.

In general, the currently proposed gastric electrical stimulation procedures are relatively invasive and require accessing the stomach through the abdomen, e.g., in an open or a laparoscopic procedure. The units have relatively wide dimensions in one plane. Accordingly, it would be desirable to provide a less invasive procedure and device for electrically stimulating the stomach. It would also be desirable to provide a device in which various components are accessible for removal or replacement, particularly in a less invasive procedure.

A machine that places a nylon tag has been proposed for attaching a "payload" to the inner wall of a stomach. The machine places the tag through the stomach wall and back into the stomach in a manner that causes folding of the stomach wall and may cause tissue damage when the smooth muscle of the stomach wall contracts. It would therefore be desirable to provide a means and method for implanting, a functional device having therapeutic or diagnostic functions, within the stomach wall, so that the stomach wall is protected from damage from mechanical stresses and forces due to the attachment of the stimulator device. It would further be desirable to employ such device and method that at the same time protect the functional device from the stomach's corrosive environment, or churning or grinding forces, and peristaltic movement, typical when food is digested and passed out of the stomach into the intestinal tract.

SUMMARY OF THE INVENTION

The present invention provides a device, system and method for diagnosing and treating gastric disorders. The present invention further provides a device, system and method for gastric electrical stimulation. The therapeutic or diagnostic device of the present invention resides within or on the patient's stomach wall.

A functional device is provided that may be endoscopically attached to the inner stomach wall. The functional device may have one or more therapeutic or diagnostic functions. The device may be used for long or short term monitoring or therapies of gastrointestinal and other physiological and clinical conditions. The device can be used for diagnostic or therapeutic applications such as pH monitoring, pressure monitoring, temperature monitoring, electromyogram, recording, electrogastrogram recording, electrical stimulation, gastric pacing, substance or drug delivery (e.g. medication or gene therapy), balloon obesity therapy, etc. Various sensors may be used, e.g., a pressure sensor, a strain gauge, a temperature sensor, a pH monitor, a sensor for sensing muscle contractions of the stomach, a sensor for sensing electrical parameters of the stomach wall, a glucose monitoring, or redox. The sensors may be used to sense electrical parameters, pressure, movement, temperature. Diagnostic ultrasound may be utilized by an implanted device with an acoustic transducer. Other parameters may be measured to determine conditions of the stomach or effectiveness of treatment such as electrical stimulation. The device may be used to treat various stomach conditions including gastric motility disorders, to deliver drugs or substances at a desired or predetermined rate (e.g. a slow release or localized drug treatment), and/or to treat obesity, to name a few applications. The device may be used for electrical stimulating a muscle layer of the stomach wall or associated nerves of the stomach. An externally transmitted telemetric signal may be used to actuate treatment. For example, the release of the medication or other substance may be actuated by an external RF signal received by electronics in the device housing. Sensed diagnostic information may also be transmitted from the implanted device to an external receiver/controller that may record or evaluate the sensed information.

Electrical stimulation is generally defined herein to mean any application of an electrical signal or of an electromagnetic field to tissue of the stomach for a therapeutic or diagnostic purpose. In one embodiment, an electrical stimulation signal entrains a slow wave signal of the stomach smooth muscle that is clinically absent, weak or of an undesirable frequency or repetition rate, is sporadic or otherwise not optimal. Also the stimulator may be designed to trigger the spike burst electrical activity of the smooth muscle associated with smooth muscle contractions. The signals may also be designed to inhibit smooth muscle pacing potentials to reduce smooth muscle contractions. The signals may also be designed to disrupt the natural waveform and effectively alter the existing or inherent pacing. The stimulator may also be designed to affect nerves associated with the stomach. In one variation, the device is designed to facilitate or expedite mixing or breaking down of food matter or liquids in the stomach. In another variation, the device is designed to control, facilitate or expedite movement of food matter or liquids through the stomach and into the small intestine. In another variation, the device is designed to stimulate the stomach to delay passage of food from the stomach and into the small intestine. Other stimulation effects are also contemplated, including but not limited to using stimulation to treat nausea, obesity or pain symptoms. The stimulation may affect the smooth muscle contractions and/or nerves associated with the stomach.

The stimulation electrodes provide stimulation either by way of a preprogrammed pulse generator or one that is programmed or revised when the device is implanted in the stomach, e.g. based on sensed parameters or response to stimulation and/or to optimize various parameters, e.g., impedance, current density, etc. The stimulator is preferably provided with RF or other signal transmission and reception capabilities. The signal transmission capabilities may be used for telemetric communication between the stimulator and an external device, e.g. to communicate data to the external device or to receive additional programming information, command signals or stimulation signals from the external device. The stimulator may also combine the electrical stimulation feature with other therapeutic or diagnostic functions such as, e.g., drug delivery.

One embodiment of the device includes: an electronics unit containing the electronic circuitry of the device with at least one stimulating electrode that when implanted is in electrical contact with a muscle layer of the stomach wall.

One embodiment of the device includes: at least one stimulating electrode in electrical contact with the stomach wall; an electronics unit containing the electronic circuitry of the device; and an attachment mechanism for attaching the device to the stomach wall. One or more stimulating electrodes may be secured to the wall of the stomach by the attachment device. One or more stimulating electrodes may also be located on the electronics unit housing. In one embodiment, at least one stimulating electrode is embedded in the wall of the stomach. Alternatively a housing may be removably attached to the stomach wall and removably connected to an electrode portion implanted in the stomach wall. The housing or unit containing batteries, electronics or other features, thus may be exchanged while the electrode portion or other portions remain implanted in the stomach wall, e.g. when the batteries need replacement.

The stimulation is provided through at least one stimulating electrode and preferably through at least one pair of bipolar electrodes. Alternatively a remote return electrode may be provided in a monopolar device. The stimulator device may be powered by a battery included with the device or may be inductively powered, e.g. by an external source.

The stimulation device is constructed of a size and shape such that it can be deployed through the mouth and esophagus with the aid of an endoscope. As such, the stimulator is of a generally small profile, e.g. a cylindrical shape, when delivered to the implant site.

The functional device of one embodiment includes a chamber for receiving tissue of the stomach wall to which the device is to be attached. Suction is applied to the chamber to draw tissue into the chamber for attaching the device. An attachment mechanism pierces the tissue of the stomach wall to attach the device. In one variation, the attachment mechanism pierces the entire stomach wall and returns back through the stomach wall. In another embodiment, the attachment mechanism pierces a portion of the stomach wall. The attachment mechanism may include a needle or one or more prongs. In some variations of the invention, for example, the attachment mechanism may be advanced distally to pierce the stomach wall, it may be drawn proximally to pierce the stomach wall or it may rotate through the chamber to pierce the stomach wall. In another embodiment, the vacuum chamber is not incorporated into the implant but rather is part of the endoscopic delivery device.

The housing of one embodiment includes a battery, electronics, a vacuum chamber, a vacuum line, needle guide hole, and one or more anchor needles. Each anchor needle includes one or more electrodes, which are connected to the electronics and battery. When the anchor needle or prong engages the tissue the electrode or electrodes are in electrical contact with the tissue. The housing also includes a connector, which can be held or released by an endoscopic connector tool. The electrical stimulation pulses of the device are delivered through an electronic circuit in the housing that is electrically coupled to the electrode(s). The stimulation parameters of the device can be programmed using an external programmer via telemetry.

The attachment mechanism is locked into place by various possible mechanisms, including, for example by magnetically coupling or locking the attachment device in place. Other locking mechanisms may be used. The locking mechanism is easily released so that the device may be easily removed relatively atraumatically when desired (e.g., days, weeks, months or years after implantation.)

In another embodiment, the device functions as an anchoring device and has a housing containing a suction chamber an attachment mechanism, e.g., an anchor, prong or needle. Where the functional device is a stimulator, the attachment mechanism may carry one or more electrodes. The anchoring device can be anchored to the stomach wall, but may or may not have additional functionality. Functionality beyond that of the anchoring device may be provided by separate modules that can be endoscopically attached to or removed from the anchoring device. Such a module may contain electronics and/or batteries and the housing and contacts on the module that align and engage when the module is attached to the housing. Change of electronics of battery may thus be accomplished by a simple endoscopic procedure. The modules may be used where there is a long-term power requirement, or in other applications where a component may need to be replaced periodically. For example, different types of modules with different functional attributes may be attached. A drug delivery reservoir may be contained in a removable replaceable module. Certain functional modules may become outdated or improved and it may be desirable to upgrade.

A functional device of the invention may be a drug delivery device. The device is attached to the stomach wall and a drug pump is actuated by an electronic control signal delivered by electronic circuitry to the pump. The drug may be pumped into the stomach itself, into the stomach wall or externally of the stomach wall or any combination of the foregoing. The electronic circuitry may be preprogrammed to control drug or substance delivery according to a certain regimen. It may also determine its regimen based on sensed feedback. Also the parameters of the drug deliver or the control of the delivery itself may be actuated by an external control signal or by an external controller that programs the electronic circuitry via a telemetric communication.

The device components are constructed of biocompatible materials that allow it to withstand and function in the highly acidic environment of the stomach (the pH in the stomach may be, at times, as low as 1.0), or, within the stomach wall for the life of the device, e.g., several weeks, months or more. The housing of the electronics unit or shell may be constructed with medical grade titanium, tantalum or alloys of these metals, which where exposed to the acidic stomach conditions, are relatively inert to the environment. Alternatively, the housing may also be constructed out of suitable inert polymers, for example, from the polyolefin family, e.g., HDPE (high density polyethylene), LLDPE (linear low density polyethylene), and PP (polypropylene), UHMWPE (ultra high molecular weight polyethylene), or fluoropolymer such as PTFE (polytetrafluoroethylene) FEP-fluorinated ethylene propylene) and other members. PMP (polymethylpentene), polysulfone, PMMA (polymethylmethacrylate) may also be used. Block copolymers may also be used or selected according to desired properties. Softer materials may be used, such as, e.g., silicones, C-Flex™, polyurethanes, co-polymer nylons (e.g. PEBAX).

The electrodes are preferably made of corrosion resistant metals and alloys such as, e.g. platinum, iridium, gold, tantalum, titanium, stainless steel or alloys of one or more of these metals, e.g., a platinum/iridium alloy.

The electrodes may be mounted directly on the housing, the attachment device, or placed on a flexible tail or tether. The electrodes are preferably coupled to the electronic circuitry through sealed electrical contacts or through leads extending into the housing through molded corrosion resistant materials such as those described above.

A preferred system of the present invention includes an endoscopic delivery system for delivering the stimulator through the esophagus and into the stomach where it is attached to or implanted in the stomach wall.

One embodiment of the system includes a flexible endoscope or endoscopic instrument, for locating a preferred site in the stomach for device attachment. In one embodiment, the endoscope or endoscopic instrument comprises electrodes that may be placed on the inside of the stomach wall to measure electrical activity or impedance, or to deliver test stimulation pulses to identify optimal stimulation parameters or locations. The endoscope also provides one or more conduits through which tools for attaching the device are inserted. In addition to the device being capable of stimulating the stomach wall, the electrodes of the device may also be used for diagnostic purposes. For example, the electrodes may be used to sense and observe electrical activity in the stomach wall. Such sensing may be used over time to identify patterns, diagnose diseases and evaluate effectiveness of various treatment protocols. For example irregular or lack of EMG or EGG (electrogastrogram) activity may be sensed. Stimulation may be provided in response to sensed EMG or EGG activity or lack of activity.

The delivery of the device is preferably performed with the guidance of an endoscope and using instruments inserted through a port in the endoscope, an overtube, or along side of the endoscope. The device is held in place in front of the endoscope by a custom or standard endoscopic connector tool, device holding instrument, grasper, or the like. The device and endoscope are inserted into the esophagus and into the stomach. An overtube may be used with the endoscope to protect the esophagus. The overtube may also include additional instrument channels for placing instruments through the esophagus. The endoscope is steered to a position adjacent to the stomach wall for attaching the device. Various device actuation and holding instruments may be used to perform the procedure of attaching the device to the stomach wall.

A vacuum line is provided to apply a vacuum pressure to the chamber of the device to draw in a portion of the stomach wall for attachment. The attachment mechanism is then used to engage the tissue drawn into the chamber. An attachment mechanism on the functional device attaches the functional device to the stomach wall using an endoscopic tool to actuate the attachment. The endoscopic connector tool releases the anchored device and the endoscope is retracted.

In one variation, sensors can be included in the device or separately for sensing various parameters of the stomach. The sensors may be mounted on the electronics unit (stimulator housing), an attachment mechanism, or by other means, for example, in an independently attached device for example attached with an anchor or within the submucosa. The stimulation device may include a mechanical sensor that senses, for example, stomach wall contractions. In one embodiment a device implanted in the stomach wall includes a pressure sensor that is arranged to measure pressure change due to contractions of surrounding tissue. Alternatively, electrical sensors may detect changes in impedance due to changes in wall thickness from smooth muscle contractions. Other examples of such sensors may include, for example, pH sensors, impedance sensors, pressure sensors, strain gauges, and temperature measuring devices such as a thermocouple.

The stimulation device may be programmed to deliver stimulation in response to sensing electrical parameters or other sensed parameters. For example, a pH sensor may be used to determine when food has been ingested. When the pH changes in a manner, indicating food ingestion, the stimulation device may be instructed to deliver stimulation pulses to stimulate gastric motility. The device may also be user controlled, where the recipient of the device or treating practitioner is able to externally activate the device, for example by using an external unit which delivers a control signal via telemetry. A temperature sensor may be used, for example, to determine when food has been ingested, by a change in temperature. The device may begin stimulating the stomach upon detecting sudden change in temperature. Pressure sensors may be used to sense motility patterns, e.g. presence, strength or frequency of contractions. Mean pressure shifts may be observed to identify fundal contractility. The stimulation device may also use sensed parameters to program or reprogram the device stimulation program. For example, by measuring impedance changes through a circuit coupled to the electrodes (e.g., delivering a constant current or voltage across the electrodes to determine impedance) or determining the contractile behavior of the stomach using a strain gauge, in response to stimulation pulses, the effectiveness of the stimulation pulses may be monitored and adjusted to provide optimal response. The stimulation program may also include an automatic adjustment in response to changes in pressure measurement.

Other diagnostic or treatment devices may be attached to the inside of the stomach wall, for example using a separate or integrally formed anchoring device. Preferably such devices are introduced and attached to or implanted in the stomach endoscopically. Such devices may include, for example, drug delivery devices, a gastric balloon, sensing or diagnostic devices. In one embodiment when excessive acid concentration is sensed using a pH sensor, a device is triggered to release an antacid drug, e.g., using a drug delivery pump.

The functional devices may be powered by a battery included with the device or the functional devices may be inductively powered. All or a portion of the device may be removed and replaced for purposes of replacing a portion of the device, e.g., a battery unit. As such, the various modules of the device are provided with docking features.

Illustrative embodiments of various aspects of the invention are described in the following detailed description.

BRIEF DESCRIPTION OF THE DRAWINGS

FIGS. 2A–G illustrate instruments and a method for implanting the functional device of FIG. 1.

FIG. 2A is a side view of the functional device being located at a site for implantation.

FIG. 2B is a side view of the functional device with tissue drawn by vacuum into a chamber in the device.

FIG. 2C is a side view of the functional device being attached to the stomach wall.

FIG. 2D is a side view of the functional device being release from an engaging tool.

FIG. 2E is a side view of the functional device being disengaged from the vacuum line.

FIG. 2F is an expanded cross sectional view of the area designated in FIG. 2A of the expander of the engaging tool connected to the functional device.

FIG. 2G is an expanded cross sectional view of the area designated in FIG. 2D of the expander of the engaging tool disconnected from the functional device.

FIGS. 4A–H illustrate instruments and a method for implanting the functional device of FIG. 3.

FIG. 4A is a side view of the functional device being located at a site for implantation with a carriage in a closed position.

FIG. 4B is a side view of the functional device or FIG. 4A with the carriage in an open position.

FIG. 4C is a side view of the functional device with tissue drawn by vacuum into a chamber in the device.

FIG. 4D is a side view of the functional device being attached to the stomach wall.

FIG. 4E is a side view of the functional device being release from an device holding and needle actuation tool and the vacuum line.

FIG. 4F is a perspective view of the distal end of a device actuation instrument used in FIGS. 4A–E.

FIG. 4G is a side cross sectional view of the device actuation instrument of FIG. 4F in a position engaging a carriage.

FIG. 4H is a side cross sectional view of the device actuation instrument of FIG. 4F in a position in which it is inserted or removed from the carriage.

FIGS. 5A–F illustrate an alternative device implanted using instruments of FIGS. 4A–H in use with an end cap of the present invention.

FIG. 5A is a perspective view of a device being implanted with an endoscope and associated instruments with the device located within an end cap of the invention.

FIG. 5B is an exploded perspective view of the device, endoscope, instruments and end cap of FIG. 5A.

FIG. 5C is a top view of the device, endoscope, instruments and end cap of FIG. 5A.

FIG. 5D is a side cross sectional view of the device, endoscope, instruments and end cap of FIG. 5A.

FIG. 5E is a side view of the endoscope, and end cap of FIG. 5A in use in attaching the device to a stomach wall.

FIG. 5F is a side view of the endoscope, instruments and end cap of FIG. 5A after attaching the device to a stomach wall.

FIG. 10A is an exploded perspective view of a functional device with removable replaceable modules and an endoscopic delivery instrument.

FIG. 10B is a perspective view of the functional device and instrument of FIG. 10A.

FIGS. 10C–E are side views of the device of FIG. 10A with endoscopic instruments for removal of a module of the device in a procedure in which the module is removed.

FIG. 12A is a cross sectional view of a drug delivery device of the present invention attached to a stomach wall.

FIG. 12B is a detailed view of one alternative embodiment of the area x of the device illustrated in FIG. 12A.

FIG. 12C is a detailed view of another alternative embodiment of the area x of the device illustrated in FIG. 12A.

FIG. 12D is side cross sectional view of alternative embodiment of a drug delivery device of the invention.

DETAILED DESCRIPTION OF THE DRAWINGS

According to one embodiment of a method of the invention, an endoscope and associated instruments are used implant a functional device through a patient's mouth, and esophagus into the stomach of a patient. In one embodiment, the instruments are used to attach the device at the selected site of the stomach wall. According to one variation suction is used to stabilize or hold the tissue of the stomach wall during the attachment procedure. In one embodiment a stimulator device is attached to the stomach wall with stimulation electrodes in electrical contact with the stomach wall. Various embodiments of the method for implanting a functional device in the stomach wall will be evident from the description of the implants and instruments below.

Figure 17:
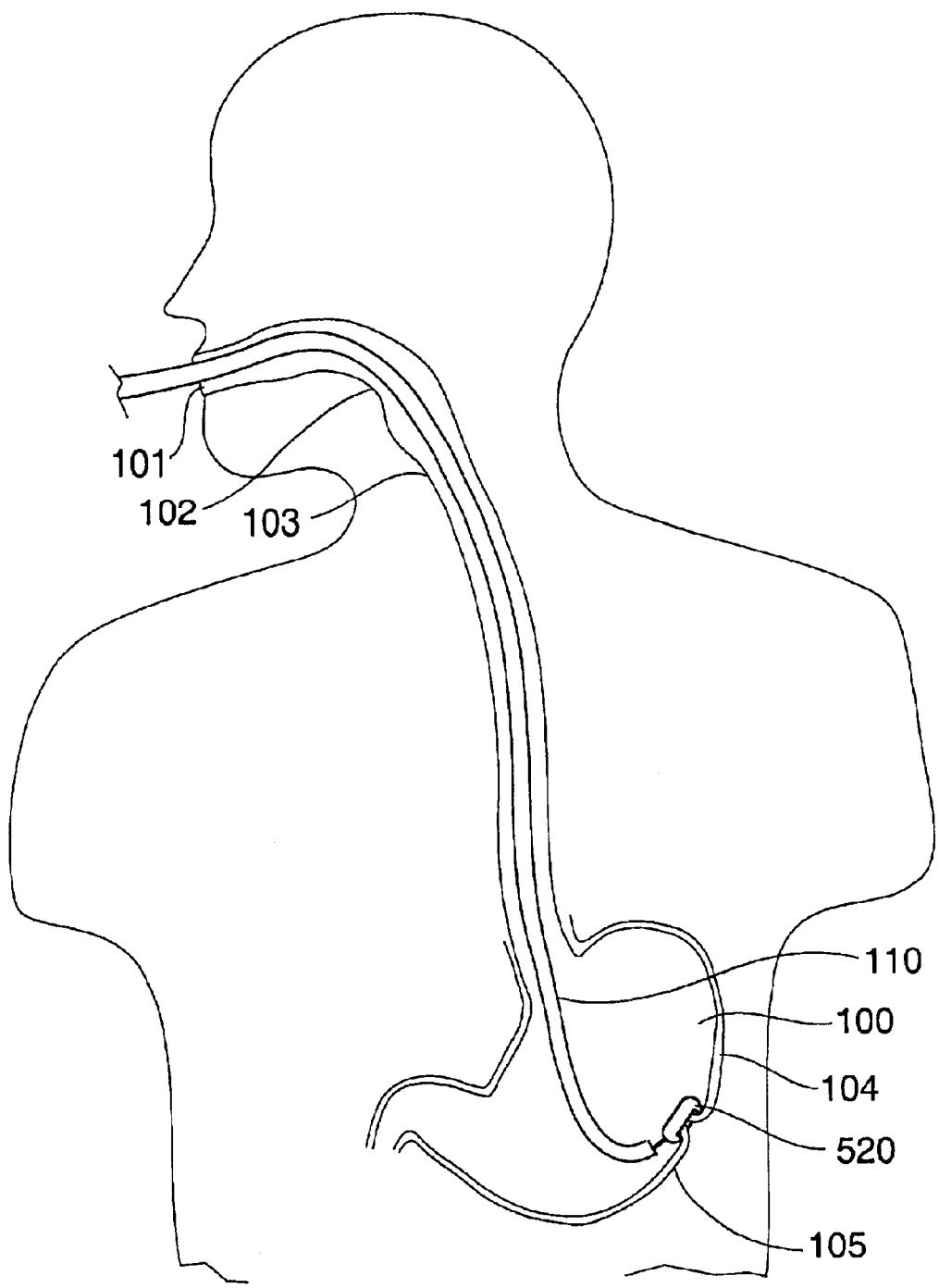
FIG. 17 is a partial cross sectional view of a system of a first embodiment of the present invention in use in implanting a functional device in a patient's stomach.

As illustrated in FIG. 17, to implant the device in the stomach, an endoscope 110 is used with various instruments as will be described in more detail below. A flexible endoscope 110 is used to locate an implantation site 105 within the stomach 100 and implant the stimulator device 520 (or devices 560, 560a, 605, 610, 620, 660, 690, 710, 730 or 750) at the site 105 within the stomach wall 104 of a patient. The flexible endoscope 110 may be of the type that is typically used by gastroenterologists in treating the upper gastrointestinal tract and in accessing the esophagus or stomach. The endoscope allows the physician to visualize while performing procedures on the upper gastrointestinal tract. The flexible endoscope may be, for example, a flexible fiber optic endoscope utilizing optic fibers for imaging or a video endoscope that uses a CCD (charge coupled device) to provide video images. Such endoscopes typically include a fiber optic light guide and a complex objective lens at the distal end to focus the image.

Figure 18A:
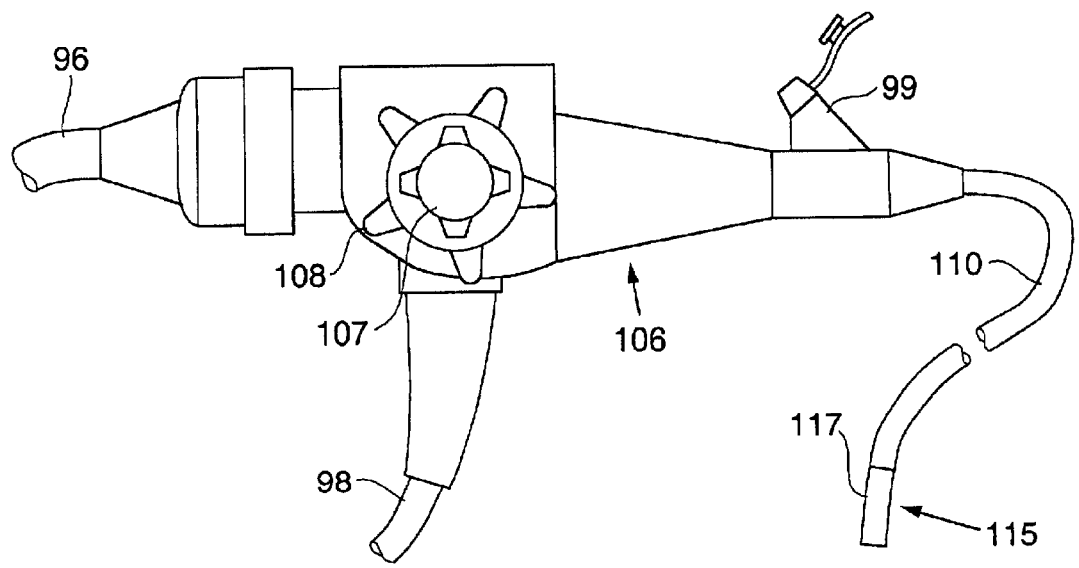
FIG. 18A is a side view of an endoscope to be used according to the present invention.
Figure 18B:
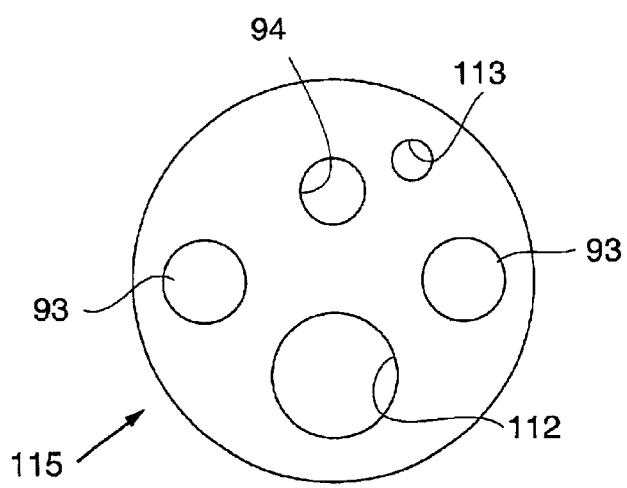
FIG. 18B is a front view of the distal end of an endoscope to be used according to the present invention.

As illustrated in FIGS. 18A–18B, the endoscope 110 comprises an elongate tube having a proximal handle portion 106 and a distal portion 115. The endoscope includes an aspiration/instrument channel 112 and irrigation/air channel 113. The aspiration/instrument channel 112 maybe used for instruments if not otherwise required in a procedure. The aspiration/instrument channel 112 extends through the endoscope 110 and provides an opening through which surgical instruments may be inserted to reach the site 105. The instruments described with respect to the various embodiments herein may be introduced through the aspiration/instrument channel 112, through an opening in an overtube, or alternatively, the instrument may be inserted along side of the endoscope 110, for example in an attached guide or sheath. Fiber optic light sources 93 for illuminating the stomach site, extend through a fiber optic channel. A video lens 94 is located at the distal end of the endoscope, for receiving and focusing the image that is transmitted back through a channel in the endoscope 110. Corresponding video output 96, ports 98 for light source input, irrigation, and aspiration and port 99 for instruments, are located on the proximal handle portion 106. Knobs 107 and 108 are coupled at the proximal handle 106 for left/right and up/down steering mechanisms, respectively, that are used to steer the distal portion of the endoscope in a manner that is generally known to one of ordinary skill in the art. The distal portion 115 of the endoscope 110 includes a steerable distal end 117.

During the procedure the patient is given a numbing agent that helps to prevent gagging. As shown in FIG. 17, the endoscope 110 is passed through the mouth 101, pharynx 102, into the esophagus 103 and into the stomach 100. If desired, an overtube may be used to protect the esophagus, which may become irritated with repeated insertion and removal of instruments. The overtube may also help prevent instruments and devices from inadvertently dropping into the trachea. In addition, an overtube may serve to protect the tools from the bacteria in the mouth and esophagus so that such bacteria are not passed on to the stomach wall. The overtube may also include additional channels for inserting additional instruments. As an alternative to an overtube, additional instruments may be attached to the outside of the endoscope and inserted through the esophagus.

Preferably the instruments inserted into the patient's stomach are coated with an antibacterial material, in particular, the instruments that are used to pierce or otherwise come in contact with the stomach wall. As illustrated in FIG. 17, the endoscope 110 is extended into the stomach 100 to a site 105 in the stomach 100 at which the stimulator 10 is being implanted. Additionally or alternatively, an endoscope or a tool inserted through the esophagus may be used to detect intrinsic gastric electrical activity to help pinpoint the optimal site for a stimulator and/or electrode implantation in the stomach wall. In such a case, sensing electrodes are coupled to the distal end of the endoscope or tool, with conductors extending out of the endoscope or patient's esophagus to a unit having a controller for receiving sensed electrical activity and identifying a surgical site for stimulator implantation.

Figure 1:
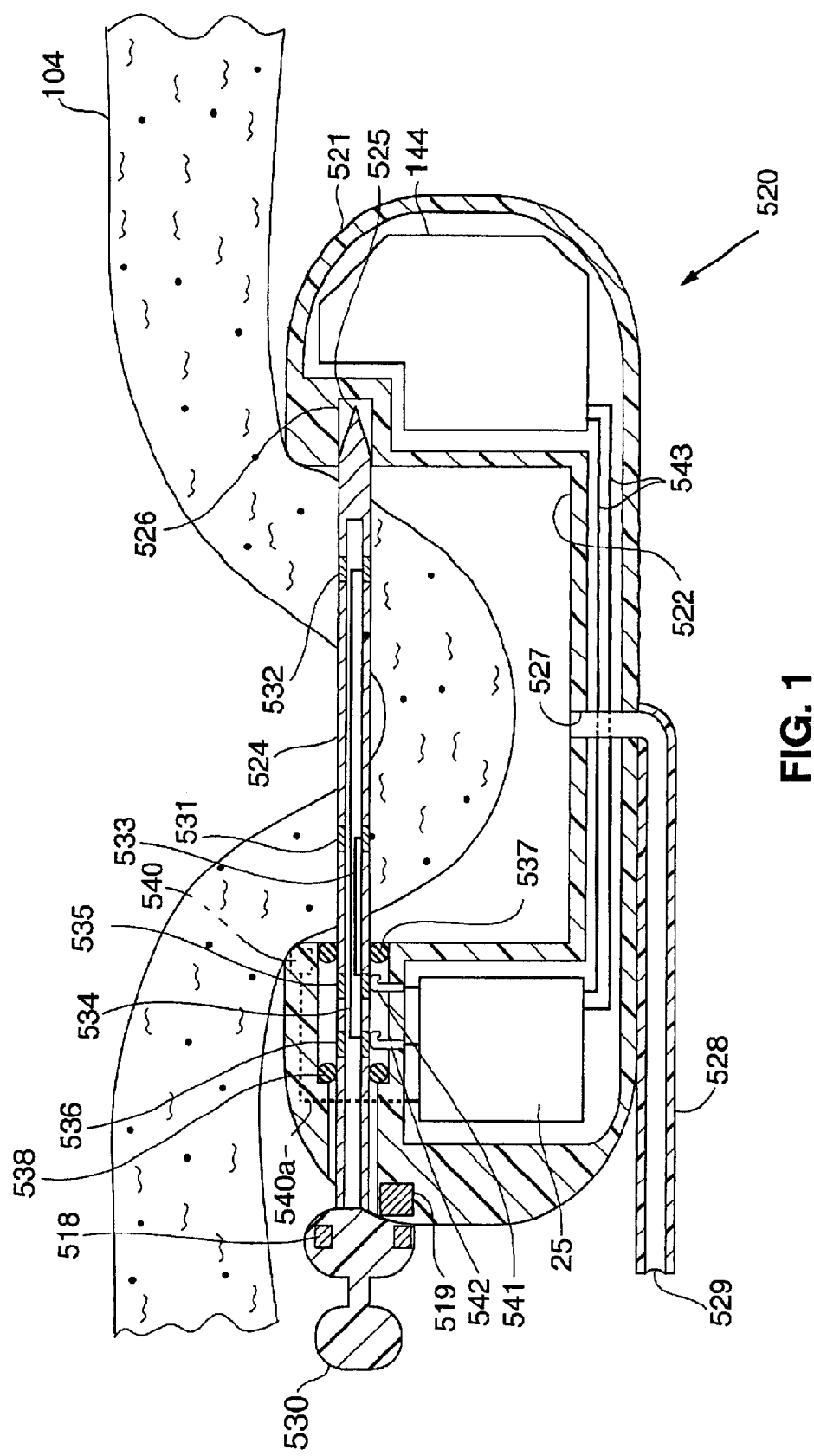
FIG. 1 illustrates a side cross section of a functional device of a first embodiment of the present invention comprising a gastric stimulator.

Referring to FIG. 1, a functional device 520 comprising a gastric stimulator is illustrated attached to the stomach wall 104. The functional device 520 comprises a sealed housing 521 including electronic circuitry 25. The electronic circuitry 25 provides sensing, stimulating electronic pulses through the electrodes to the stomach wall, and telemetry communication with an external unit such as a reader, recorder or controller. The housing may be constructed of a radiopaque material. Alternatively, the housing may include radiopaque markers located on the device so that the location and orientation of the device may be identified, particularly after it has been placed.

The housing 521 includes an open chamber 522 for receiving a portion of the stomach wall 104 for attachment. The chamber 522 includes an opening 527 coupled to a vacuum pipe 528 external to the chamber 522 of the housing. The vacuum pipe 528 has an open proximal end 529 for coupling through an elongate tube to a vacuum source.

A sliding needle 524 with a sharp tip 525 extends from a first proximal side of the device 520, distally through the chamber 522 piercing the stomach wall 104, to an opposite distal side of the device 520. A knob 530 is located on the outside of the first side of the device 520. The knob 530 enables an instrument to grasp and advance or retract the needle 524 into or from the housing 521. The knob 530 has a magnet 518 in a position adjacent the housing 521 and the housing has a magnet 519 adjacent the knob 530. The magnets 518, 519 hold the needle 524 in place when the needle 524 is in a closed position. A recess 526 in the opposite side of the chamber receives the tip 525 of the needle 524 to prevent damage and secure the needle 524 in place. Ring electrodes 531, 532 are located around the circumference of the needle 524. The electrodes 531, 532 are electrically isolated from each other and are electrically coupled to contacts 535, 536 through connectors 533, 534 extending from the electrodes 531, 532 through the needle 524 to the contacts 535, 536. When the needle 524 is in a closed position within the device 520 as illustrated in FIG. 1, the contacts 535, 536 are isolated within a space 539 in the housing 521 by seals 537, 538 that seal the space 539 from body fluids. The seals 537, 538 are preferably acid resistant elastomeric seals formed of a material such as, for example, polyurethanes, rubbers or C-Flex type block copolymers to protect the seals 537, 538 from the highly acidic environment of the stomach.

The housing 521 contains electronic circuitry 25 and a battery 144 that are coupled to each other by connectors 543. Flexible connectors 541, 542 are electrically coupled to electronic circuitry 25 and extend from electronic circuitry 25 into the space 539. When the needle is in a closed position, the flexible connectors 541, 542 are in electrical contact with contacts 535, 536 on the needle 524, and the electrodes 531, 532 are in electrical contact with the tissue of the stomach wall pierced by the needle 524. A sensor 540 is illustrated located on the housing and coupled by electrical connectors 540a to electronic circuitry 25. The sensor 540 may be located on the needle 524 as well as anywhere on the housing 521 so that the sensor 540 is able to sense a desired parameter. Various sensors may be used, such as a strain gauge, a pressure sensor, pH sensor, temperature sensor, etc. The electronic circuitry 25 and battery 144 operate to provide electrical stimulating signals to the stomach wall 104, and, optionally, telemetric communication with an external controller as described herein with reference to FIGS. 13 and 14.

FIGS. 2A–2G illustrate the device 520 shown in FIG. 1 being attached to the stomach wall by applying a suction to engage the stomach wall, and then attaching the device 520 to the engaged tissue. FIG. 2A illustrates the functional device 520 of FIG. 1 coupled to instruments extending through or alongside of an endoscope 110 and located adjacent a site 105 for attachment to the stomach wall 104. An engaging tool 550 comprises an elongate member 551 extending along side of the endoscope 110 and attached to the endoscope by a band 549. The tip 553 (FIG. 2E–G) of the engaging tool 550 is placed within a socket 523 in the housing 521 as illustrated in detail in FIG. 2F. The socket has a narrow entry 523a and a wide end 523b. A lumen 552 extends through the tool 550 ending at an opening 554 in the side of the tool at the tip 553. The tip 553 of the tool 550 is placed through the narrow portion 523a of the socket 523 in the housing 521 and into the wide end 523b so that the opening 554 opens into wide end 523b. A wire 555 extends through the lumen 552 and out of the opening 554 and into the wide end 523b at an angle. The wire is constructed of a size and material (e.g. Nitinol or stainless steel) such that it is flexible enough to turn at the angle and stiff enough to engage the housing. The wire 555 thus prevents removal of tip 553 of the tool 550 from the socket 523, thereby engaging and permitting manipulation or stabilization of the device 520, in particular axial stabilization. A grasping instrument 556 with grasping jaws 557 at its distal end extends through the endoscope 110. The grasping jaws 557 as illustrated in FIG. 2A grasp the knob 530 of the device 520 and retract the needle 524 to an open position whereby the needle 524 is retracted from the chamber 522. The open proximal end 529 of the vacuum pipe 528 is coupled to an elongate tube 558 that is coupled to a vacuum source (not shown) at the proximal end of the tube 558.

As illustrated in FIG. 2B, the chamber 522 of the device 520 is placed against the stomach wall 104 at the site 105. A vacuum is applied through the tube 558, vacuum pipe 528 and the opening 527 into the chamber 522. The vacuum draws a portion of the stomach wall 104 into the chamber 522.

As illustrated in FIG. 2C, while the engaging tool 550 holds the device in place, the grasping instrument 556 is advanced distally to move the needle 524 from an open position to a closed position in which the needle 524 extends through the chamber 522. As the needle 524 extends through the chamber 522, it pierces through the stomach wall from the inside of the stomach wall to the outside through a fold in the stomach wall 104 and back through the stomach wall to the inside of the stomach wall 104 where the needle tip 525 is placed within recess 526 and the magnets 518, and 519 magnetically engage to hold the needle 524 in its closed position (FIG. 1). In the closed position, the electrodes 531, 532 are in electrical contact with the tissue of the stomach wall 104 pierced by the needle 524. The vacuum pressure is then released.

As illustrated in FIG. 2D, with the needle 524 in place, the grasper 556 released from the knob 530 of the device 520 and the engaging tool 550 is released from the device 520. As shown in more detail in FIG. 2F, the wire 555 is retracted into the opening 554 to release the tip 553 of the engaging tool 550 from the wide end 523$b$. The elongate tube 558 is disengaged from the vacuum pipe 528 by inserting a push rod 559 through the tube 558 and vacuum pipe 528 to push off from the distal end 529 of the inside of the vacuum pipe 528. FIG. 2E shows the device 520 attached to the stomach wall 104 and disengaged from the endoscope 110 and associated instruments.

Figure 3:
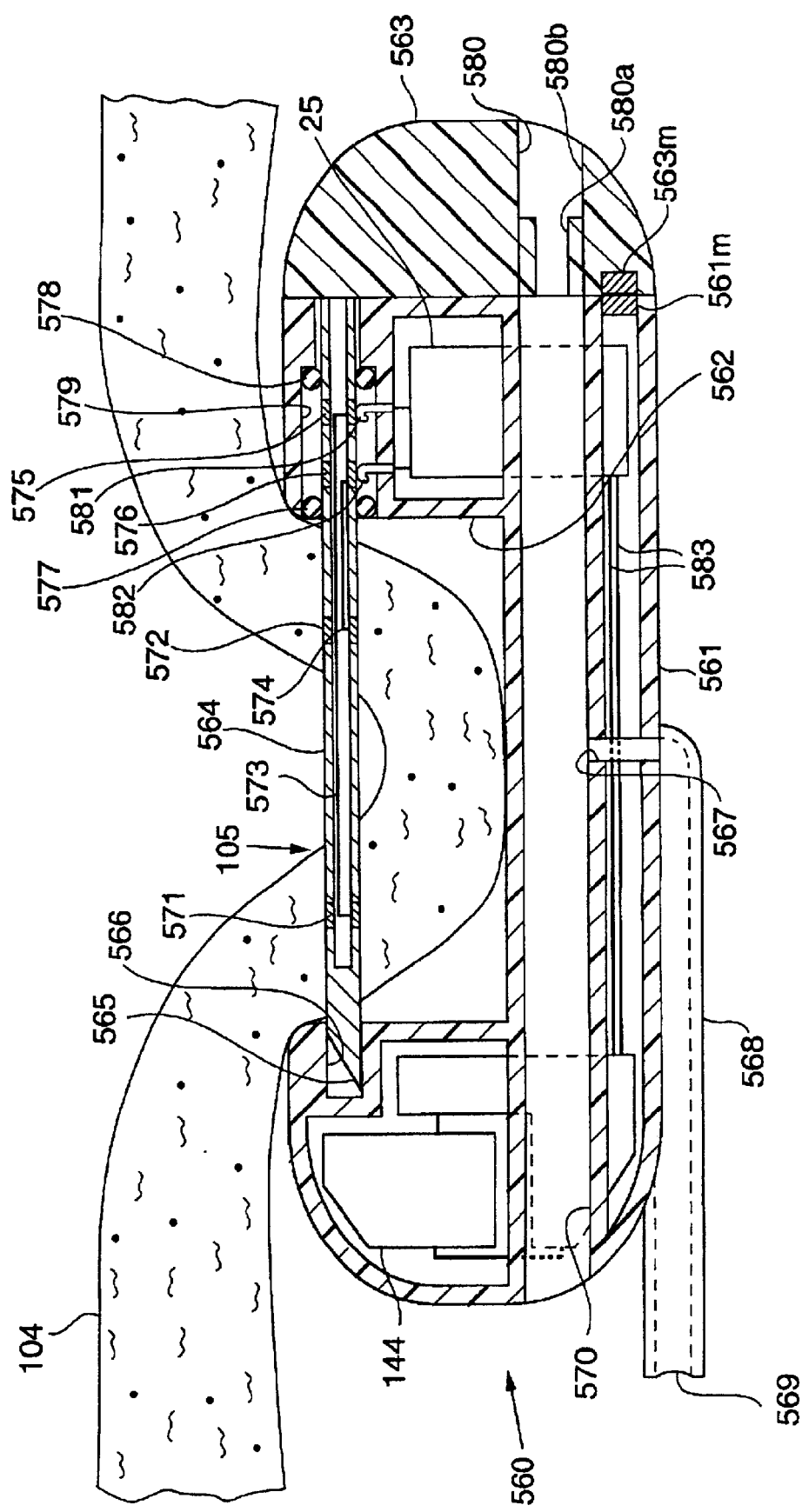
FIG. 3 illustrates a side cross section of a functional device of a second embodiment of the present invention comprising a gastric stimulator.

Referring now to FIG. 3, an alternative embodiment of a functional device is illustrated. A functional device 560 comprising a gastric stimulator is illustrated attached to the stomach wall 104. The functional device 560 comprises a housing 561 with an open chamber 562 for receiving a portion of the stomach wall 104 for attachment. The chamber 562 includes an opening 567 coupled to a vacuum pipe 568 external to the chamber 562 of the housing. The vacuum pipe 568 has an open proximal end 569 for coupling to an elongate tube to a vacuum source.

A sliding carriage 563 including a needle 564 with a sharp tip 565 extends from a first distal side of the device 560, through the chamber 562 piercing the stomach wall 104, to an opposite proximal side of the device 560. An opening 570 extending from the proximal to distal side of the housing 561 is aligned with opening 580 in the carriage 563. The openings 570, 580 are arranged to receive a device holding and needle actuation tool 590 as illustrated in FIGS. 4A–H. The tool 590 includes a means to hold the main housing 561 while advancing or retracting the carriage 563 away from or towards the housing 561, respectively. The carriage 563 has a magnet 563$m$ in a position adjacent the housing 561 and the housing 561 has a magnet 561$m$ adjacent the magnet 563$m$ of the carriage 563. The magnets 561$m$, 563$m$ hold the carriage 563 in place in a closed position with the needle 564 extending proximally through the tissue to the proximal portion of the housing 561. A recess 566 in the proximal side of the chamber receives the tip 565 of the needle 564 to prevent damage and secure the needle 564 in place. Ring electrodes 571, 572 are located around the circumference of the needle 564. The electrodes 571, 572 are electrically isolated from each other and are electrically coupled to contacts 575, 576 through connectors 573, 574 extending from the electrodes 571, 572 through the needle 564 to the contacts 575, 576. When the carriage 563 is in a closed position within the device 560 as illustrated in FIG. 3, the contacts 575, 576 are isolated within a space 579 in the housing 561 by seals 577, 578 that seal the space 579 from body fluids. The housing 561 contains electronic circuitry 25 and a battery 144 that are coupled to each other by connectors 583. Flexible connectors 581, 582 are electrically coupled to electronic circuitry 25 and extend into the space 579. When the carriage 563 is in a closed position, the flexible connectors 581, 582 are in electrical contact with contacts 575, 576 on the needle 564, and the electrodes 571, 572 are in electrical contact with the tissue of the stomach wall 104 pierced by the needle 564. The electronic circuitry 25 and battery 144 operate to provide electrical stimulating signals to the stomach wall 104, and, optionally, telemetric communication with an external controller as described herein with reference to FIGS. 13 and 14.

Figure 4A:
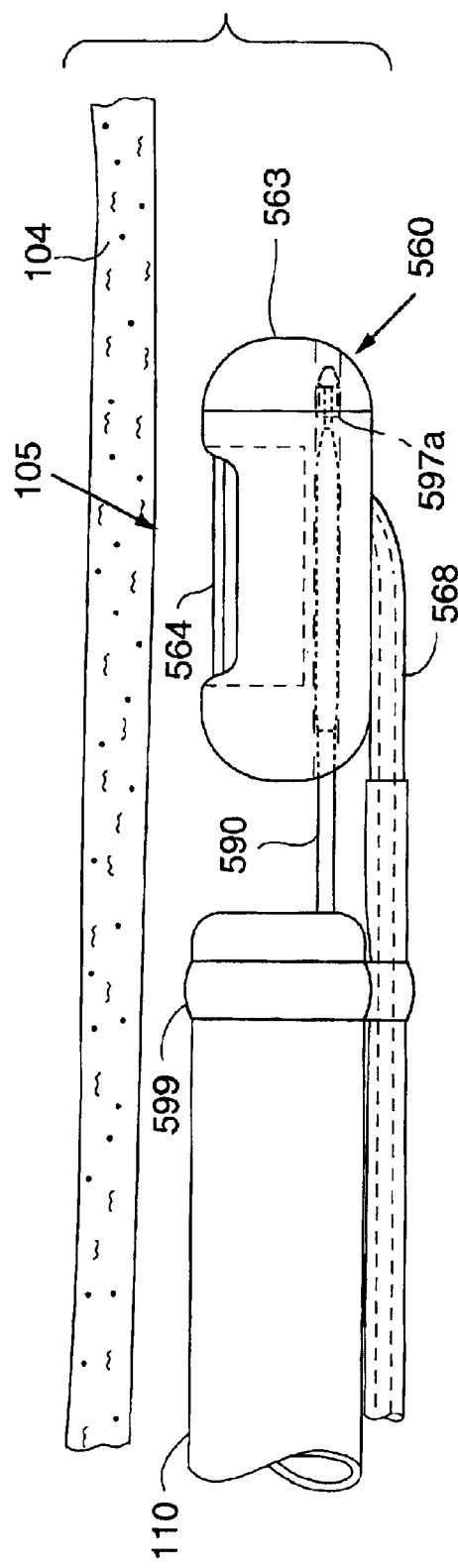

4A–H illustrate the device 560 shown in FIG. 3 being attached to the stomach wall 104 by applying a suction to engage the stomach wall and then attaching the device 560 to the engaged tissue. FIG. 4A illustrates the functional device 560 of FIG. 3 coupled to instruments extending through or alongside of an endoscope 110 and located adjacent a site 105 for attachment to the stomach wall 104. The open proximal end 569 of the vacuum pipe 568 is coupled to an elongate tube 558 that is attached to the endoscope 110 by a band 599. The elongate tube 558 is coupled to a vacuum source (not shown) at the proximal end of the tube 558.

A device holding and needle actuation tool 590 comprises an elongate member 591 extending through the endoscope 110. The tool 590 comprises a needle actuation rod 596 slidably extending coaxially through a lumen 595 in the elongate member 591 through the distal end of the elongate member 591. The rod 596 has a tapered catch 597 located on its distal end for engaging the carriage 563 as described below with reference to FIGS. 4F–H. The tool 590 includes a balloon 593 on its distal end in fluid communication with an inflation lumen 594 extending through the elongate member 591 for delivering an inflation medium to the balloon 593. In FIG. 4A, the tool 590 is placed so that the balloon 593 is located within the opening 570 in the housing 561 of the device 560. The distal end of the rod 596 is placed within the opening 580 in the carriage 563. The opening 580 has a narrower entry 580$a$ and a wider end 580$b$. As illustrated in FIGS. 4F–H the tapered catch 597 has a wide profile (FIG. 4G) and a narrow profile when the rod 596 is rotated 90 degrees. As illustrated in FIG. 4H the tapered catch 597 is oriented to fit through the narrower opening 580$a$. The tapered catch 597 of the rod 596 is placed through the narrower entry 580$a$ and into wider end 580$b$. A bumper 597$a$ is located proximally of the tapered catch on the rod 596 so that when the tapered catch 597 is advanced through the opening 580, the bumper 597$a$ engages the inside wall of the carriage 563 to advance the carriage 563 and to prevent the tapered catch from advancing too far. As illustrated in FIG. 4G, the tapered catch 597, inserted through opening 580a into end 580b, is rotated 90 degrees so that the tapered catch 597 engages the distal wall of the narrow portion 580a thereby engaging the carriage 563.

As illustrated in FIG. 4A, the balloon 593 is inflated within the opening 570 to engage the housing 561 of the device thereby permitting manipulation or stabilization of the device 560, in particular axial stabilization. The tapered catch 597 is placed in a position engaging the carriage 563.

Figure 4B:
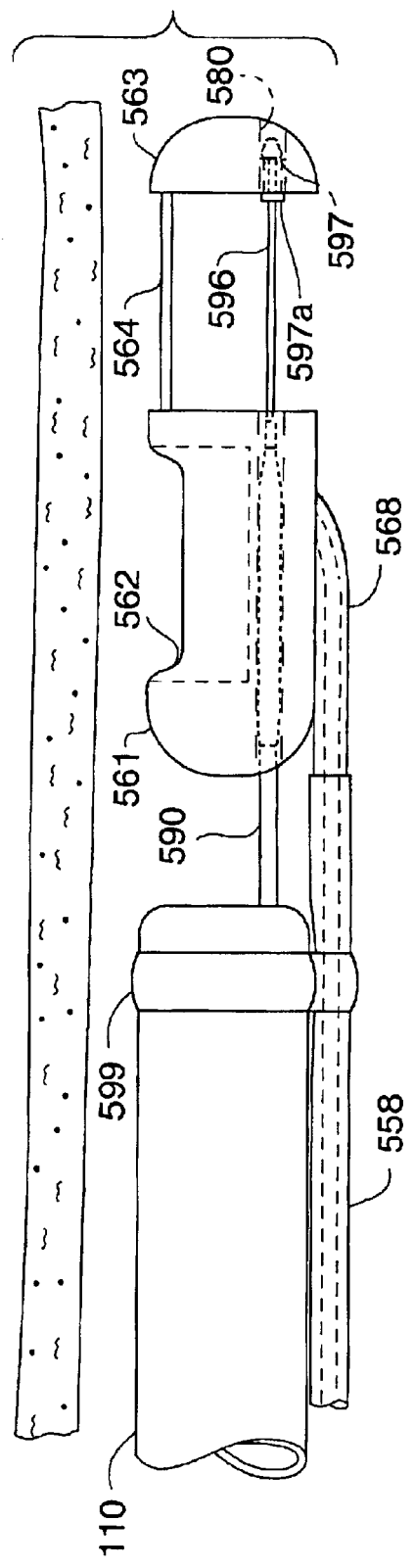

The rod 596 as illustrated in FIG. 4B is advanced distally thereby opening the carriage 563, moving the needle 564 out of the chamber 562 and opening the chamber 562 to receive tissue therein.

Figure 4C:
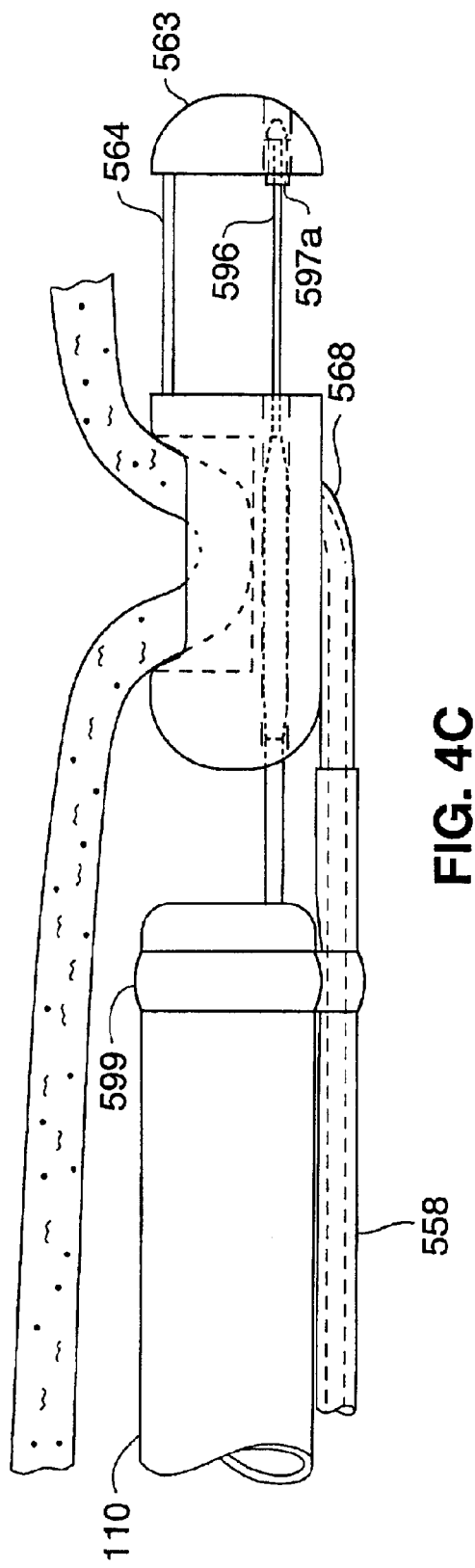

As illustrated in FIG. 4C, the chamber 562 of the device 560 is placed against the stomach wall 104 at the site 105. A vacuum is applied through the tube 558, vacuum pipe 568 and the opening 567 into the chamber 562. The vacuum pressure draws a portion of the stomach wall 104 into the chamber 562.

Figure 4D:
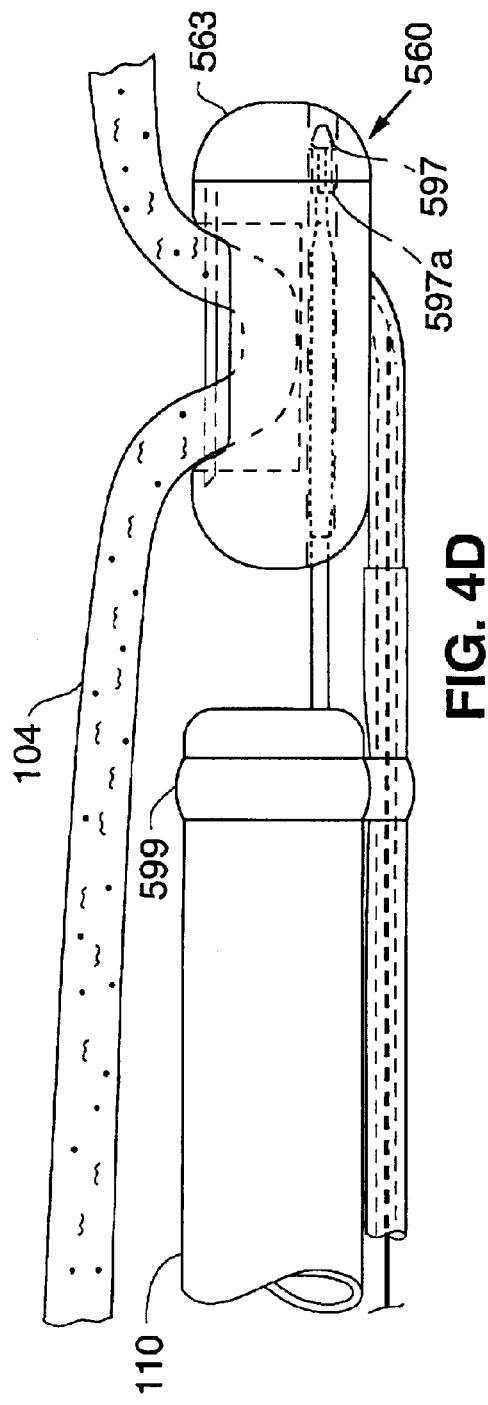

As illustrated in FIG. 4D, while the balloon 593 of the tool 590 holds the device 560 in place, the rod 596 is retracted proximally to move the carriage 563 from an open position to a closed position in which the needle 564 pierces through the portion of the stomach wall 104 located within the chamber 562. The needle 564 pierces the stomach wall 104 from the inside of the stomach wall to the outside through a fold in the stomach wall 104 and back through to the inside of the stomach wall 104 where the needle tip 565 is placed within recess 566. The magnets 561m, and 563m magnetically engage to hold the carriage 563 in its closed position against the housing 561 (FIG. 3). In the closed position, the electrodes 571, 572 are in electrical contact with the tissue of the stomach wall 104 pierced by the needle 564. The vacuum pressure is then released.

Referring to FIG. 4E, the tool 590 is released from the housing 561 by deflating the balloon 593 and rotating the rod 596 to release the catch 597 from the distal wall of the narrower portion 580a of the opening 580, withdrawing the rod 596 into the lumen, and removing the tool 590 from the openings 570, 580. The elongate tube 558 is disengaged from the vacuum pipe 568 by inserting a push rod 559 through the tube 558 to push off from the vacuum pipe 568.

Referring to FIGS. 5A–F a device 560a is implanted using the instruments of FIG. 4A–H and in addition using a auxiliary cap 600 mounted on the distal end 115 of the endoscope 110. The device 560a is similar to FIG. 3 except for the geometry of the chamber 562a which has a larger opening in the housing 561a than the chamber 562 of device 560. The cap 600 is formed of a clear material through which the endoscope 110 may visualize surrounding areas. The cap 600 is a relatively cylindrical member with a proximal opening 603, a distal opening 601, and a window opening 602 in the top of the cap 600 connecting to the distal opening 601.

Figure 5C:
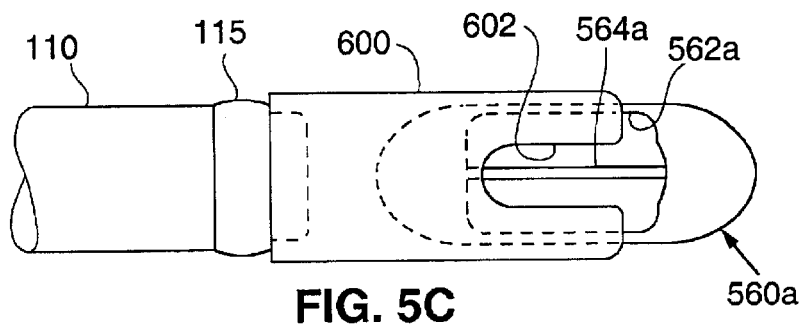

As illustrated in FIGS. 5A to 5C, the proximal opening 603 of the cap 600 is placed over the distal end 115 of the endoscope 110. The proximal end 603 of the cap 600 is press fit on to the distal end 115 of the endoscope 110. The opening 560a is inserted through the distal opening 601 into the cylindrical cap 600 with the chamber 562a opening aligned with the window 602 in the top of the cap 600. The dimensions of the window 602 in the top of the cap 600 are smaller than the opening in the chamber 562a of the device 560a.

Figure 5D:
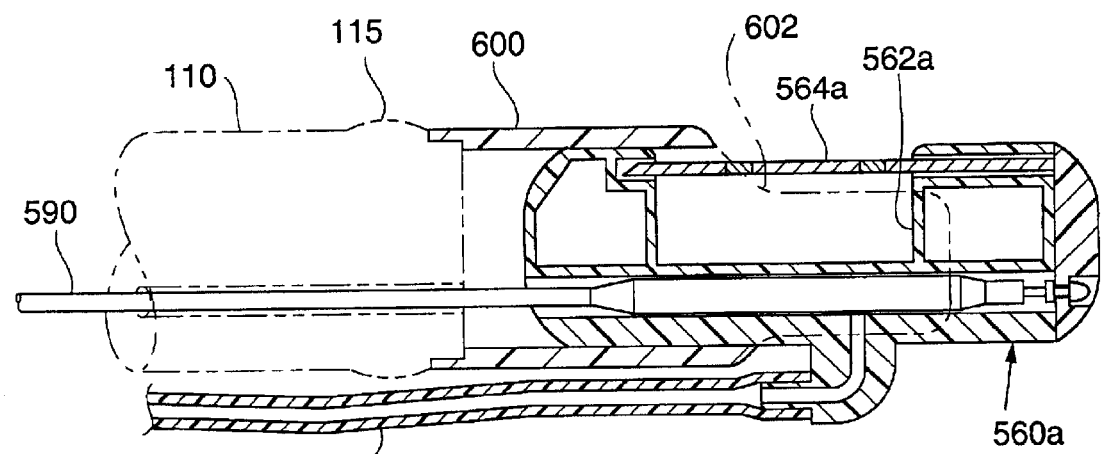
Figure 5E:
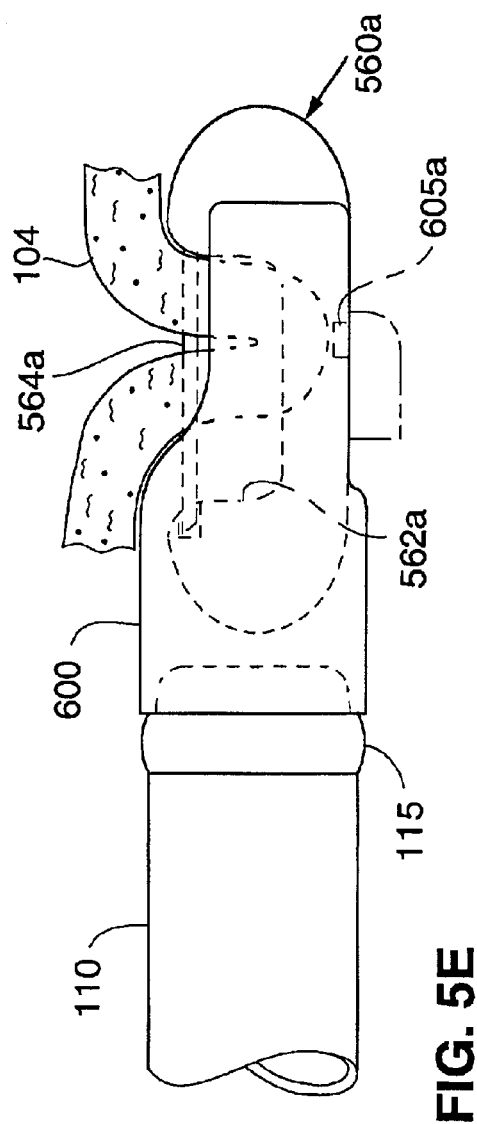
Figure 5F:
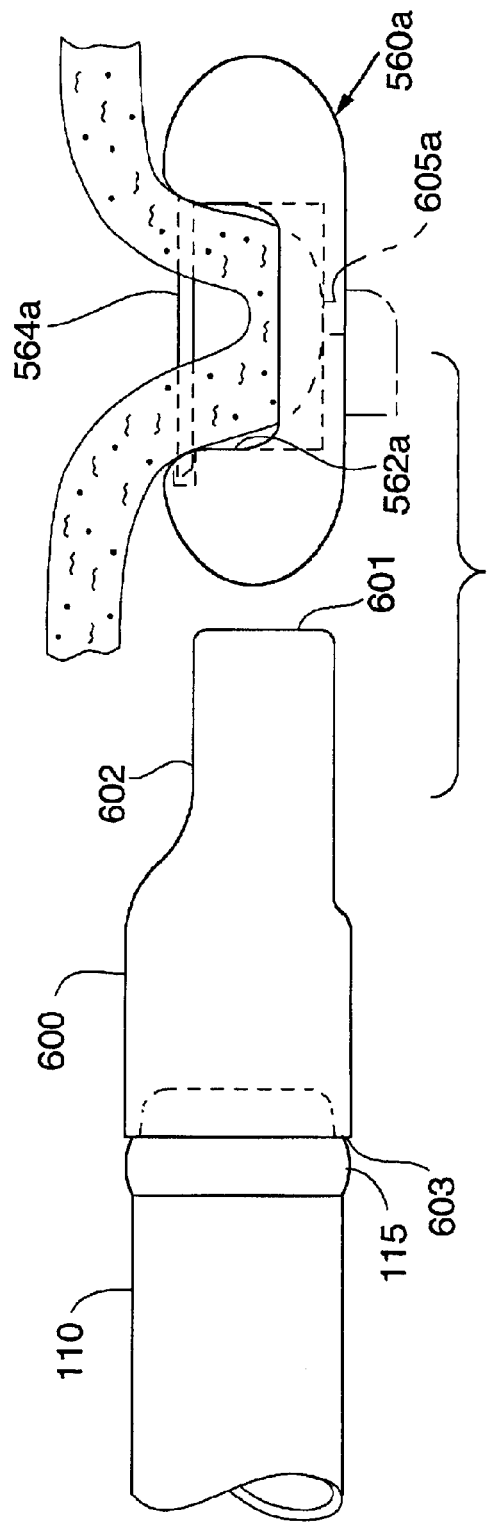

FIG. 5D illustrates the device placed within the cap 600 and coupled to endoscopic instruments. The device 560a is held by a device holding and needle actuating instrument 590, and is coupled to a vacuum source by way of elongate member 558 as described in more detail with reference to FIGS. 3 and 4A–E above. As illustrated in FIG. 5E, a vacuum is applied to a portion of the stomach wall 104 to draw tissue through window 602 and into chamber 562a. The smaller size of the window 602 holds the tissue of the stomach wall more firmly to enable the needle 564a to pierce the tissue. As illustrated in FIG. 5F, when the device 560a is released from the endoscope 110 and associated instruments, the larger sized opening in the chamber 562a allows the tissue to relax, causing less stress or pinching to the tissue.

Figure 6A:
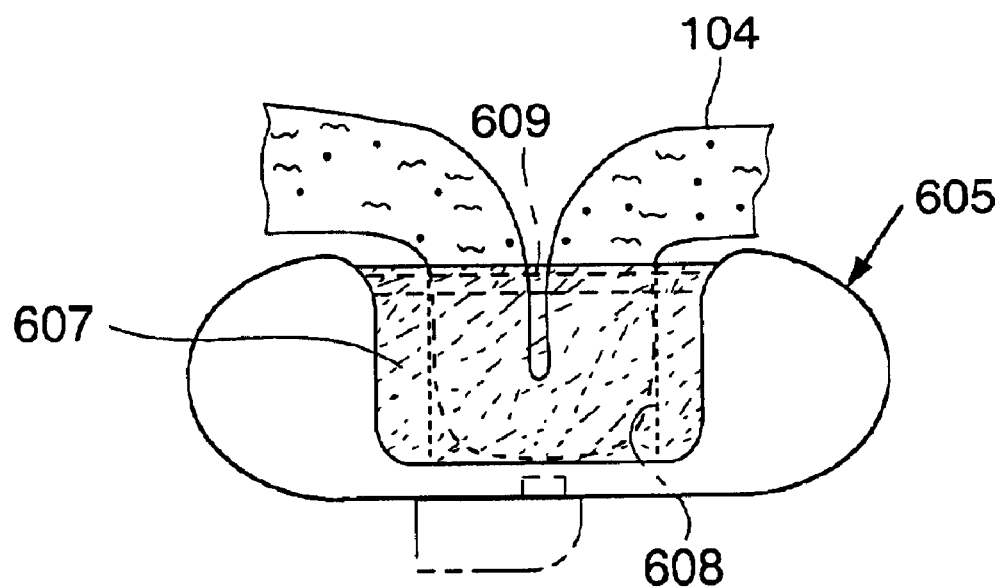
FIG. 6A is a side view of an alternative embodiment of the invention with a dissolvable material in the chamber containing a portion of the stomach wall.
Figure 6B:
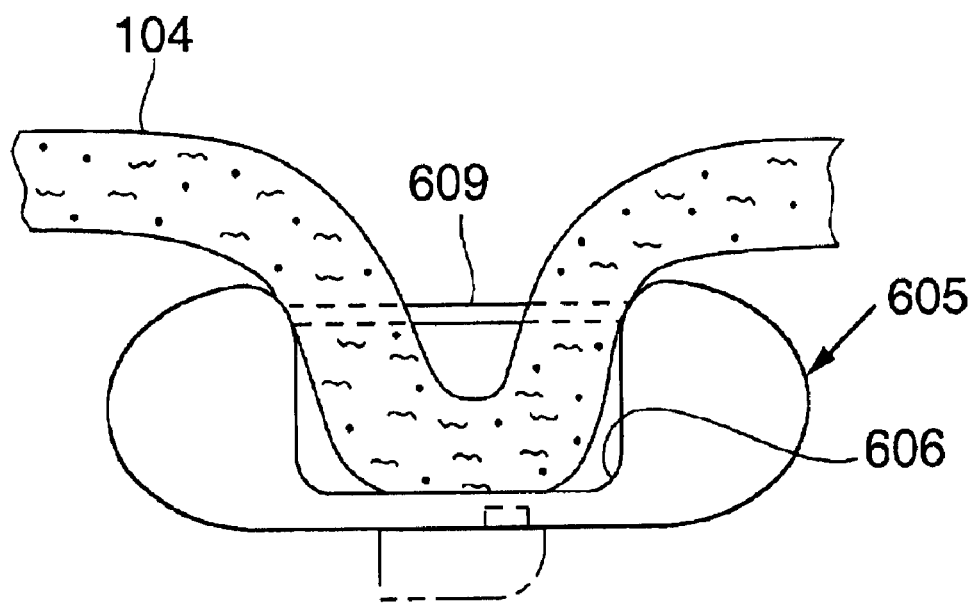
FIG. 6B is a side view of the device of FIG. 6A attached to the stomach wall with the dissolvable material dissolved.

Referring to FIGS. 6A and 6B an alternative means is provided for drawing tissue to attach the device and subsequently relaxing the tissue to reduce stresses or pinching to the tissue. The device 605 is constructed in a manner similar to the other devices described herein, such as, for example, device 520 or device 560. A chamber 606 is formed in the device 605 for receiving a portion of the stomach wall 104. In FIG. 6A, a dissolvable material 607 comprised of a medical biodegradable material, such as, for example, cellulose, polylactic acid and polyglycolic acid, forms a smaller chamber 608 within the chamber 606. A vacuum is applied through hole 605a in the device to draw tissue into the smaller chamber 608. A needle 609 is then used to pierce the stomach wall 104 tissue in the smaller chamber 608 and attach the device 605 to the stomach wall 104. As illustrated in FIG. 6B, the material 607 dissolves allowing the tissue to relax within the larger opening of the chamber 606.

Figure 7A:
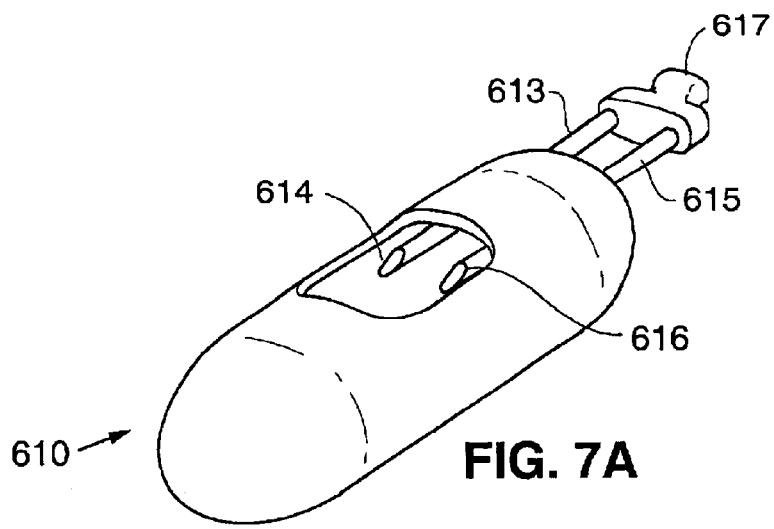
FIG. 7A illustrates a fifth embodiment of the device of the present invention.
Figure 7B:
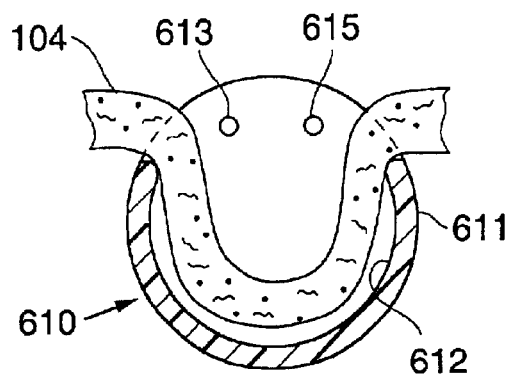
FIG. 7B is a cross section of the device illustrated in FIG. 7A.

FIGS. 7A and 7B illustrate an alternative embodiment. The stimulator 610 is constructed in a similar manner as stimulator 520 of FIG. 1 except that instead of a needle, the device comprises two prongs 613, 615 having sharp tips 614, 616 for piercing the stomach wall. In a similar manner as described above with respect to device 520, by manipulating the knob 617, the prongs 613, 615 are advanced through tissue of the stomach wall 104 drawn into the chamber 612 of the housing 611 using suction or a vacuum.

Referring to FIGS. 8A–D, another embodiment of a functional device of the invention is illustrated. A stimulator 620 comprises a housing 621 with an open chamber 622 for receiving a portion of the stomach wall 104 for attachment. The chamber 622 includes an opening 627 coupled to a vacuum pipe 628 external to the chamber 622 of the housing. The vacuum pipe 628 is arranged to couple through an elongate tube to a vacuum source.

A rotating bar 644 is rotatably coupled by way of discs 637, 638, to the housing 621 within the chamber 622. A rotating member 645 extends proximally through the housing 621 and out the proximal end 646 of the housing 621. A hex connector 647 is coupled to the rotating member 645 at the proximal end 646 of the housing 621. A hex tool may be provided, e.g., through an endoscope 110 to engage the hex connector 647 and rotate the rotating member 645 and bar 644 to move the bar from a first closed position to a second open position to attach the device 620 to a stomach wall. Alternatively, the rotating member 645 and bar 644 may be rotated from the closed position to the open position, e.g. for easy removal of the device 620. The rotating bar 644 comprises two sharp curved prongs 623, 624 having sharp tips 625, 626. The curved prongs 623, 624 are coupled to the bar 644 such that when the bar 644 rotates, the prongs 623, 624 rotate from one side of the opening 640 in the chamber 622 in a first open position (FIGS. 8A and 8C) to an opposite side of the opening 640 in the chamber 622 in a second closed position (FIGS. 8B and 8D).

Ring electrodes 631, 632 are located around circumferences of the prongs 623, 624, respectively. The electrodes 631, 632 are electrically isolated from each other and form a pair of bipolar electrodes. The electrodes 631, 632 are electrically coupled through connectors 633, 634 extending from the electrodes 631, 632 through the prongs 623, 624, respectively, to the contacts 635, 636 on disc 637. When the prongs 623, 624 are in a closed position as illustrated in FIGS. 8B and 8D, the contacts 635, 636 are in electrical contact with contacts 641, 642 respectively located on the inner chamber side wall 639 interfacing the disc 637. The housing 621 contains electronic circuitry 25 and a batteries 144 that are coupled to each other by connectors 643. Contacts 641, 642, are electrically coupled to electronic circuitry 25, by way of connectors 629, 630.

Figure 8A:
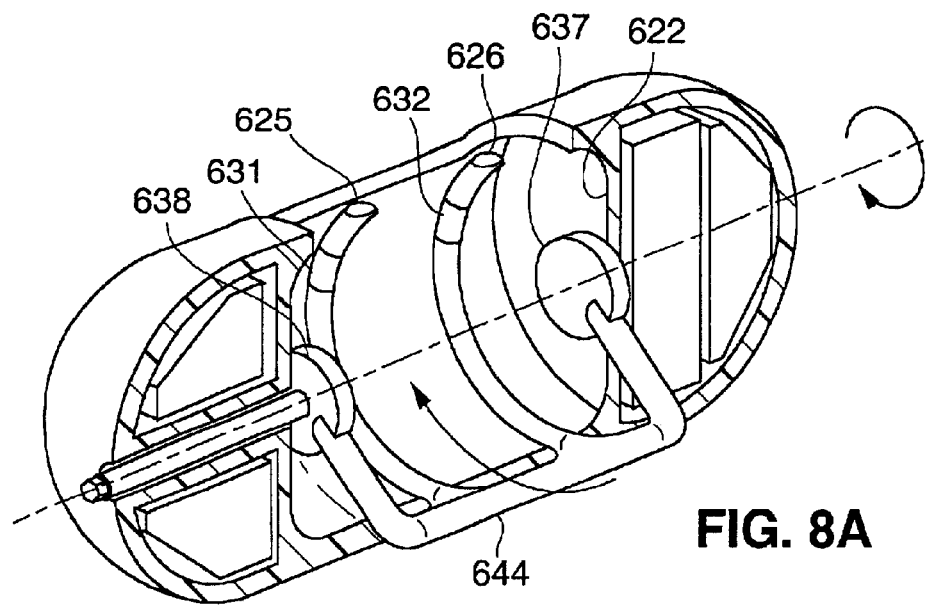
FIG. 8A is partial cross sectional perspective view of a sixth embodiment of a functional device of the present invention in a first open position.
Figure 8C:
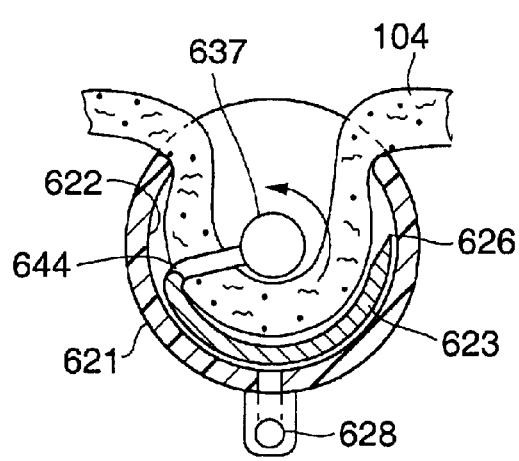
FIG. 8C is a cross sectional view of the device of FIG. 8A with tissue of a stomach wall located within a chamber of the device.
Figure 8D:
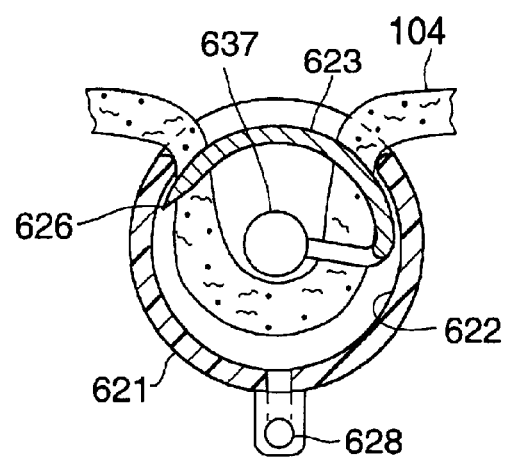
FIG. 8D is a cross sectional view of the device of FIG. 8B with tissue of a stomach wall located within a chamber of the device.
Figure 8B:
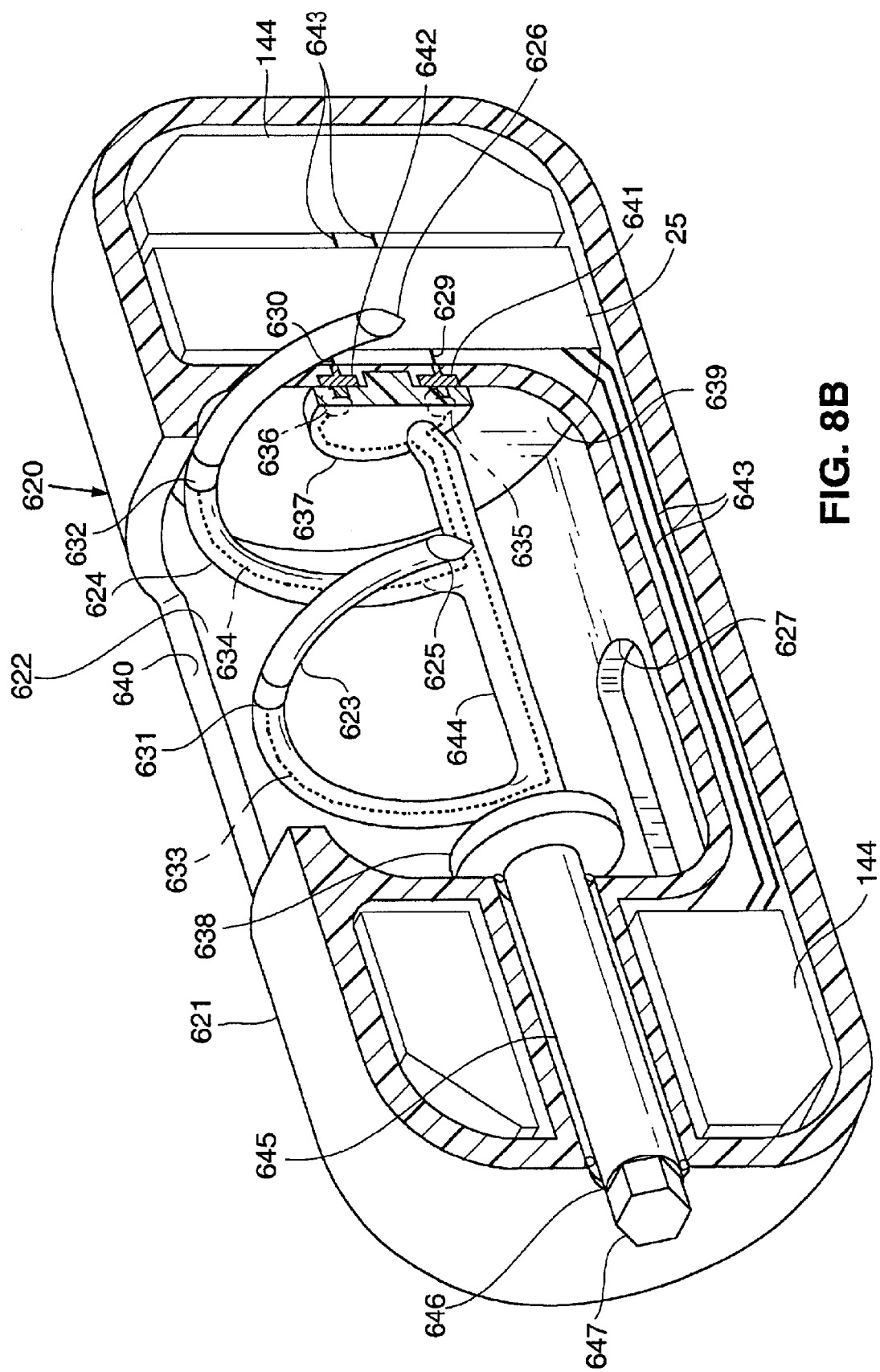
FIG. 8B is a partial cross sectional perspective view of the device of FIG. 8A in a second closed position.

FIGS. 8C and 8D illustrate the device 620 shown in FIGS. 8A and 8B with tissue of the stomach wall 104 drawn into the chamber 622 by applying a suction through the vacuum pipe 628 and opening 640 in the chamber 622, to the tissue of the stomach wall 104. In the first open position illustrated in FIG. 8C, the chamber 622 is open to receive the tissue. As illustrated in FIG. 8D, when the rotating bar 644 is rotated, the prongs 623, 624 pierce the stomach wall as they are rotated to the second closed position. When the prongs 623, 624 are in a closed position, the electrodes 631, 632 are in electrical contact with the tissue of the stomach wall 104 pierced by the prongs 623, 624. The electronic circuitry 25 and batteries 144 operate to provide electrically stimulating signals to the stomach wall 104 and optionally, telemetric communication with an external controller as described herein with reference to FIGS. 13 and 14.

Figure 9A:
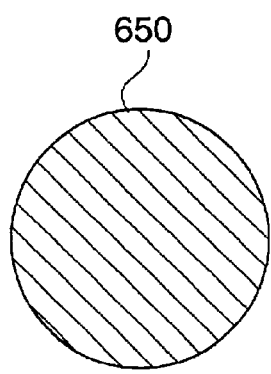
FIG. 9A–C are cross sections of various needles of the functional and anchoring devices of the invention.
Figure 9B:
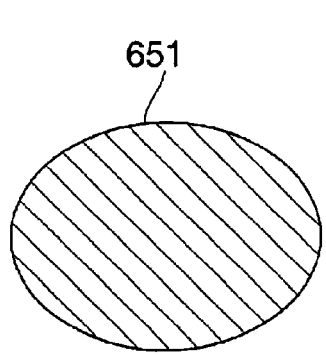
Figure 9C:
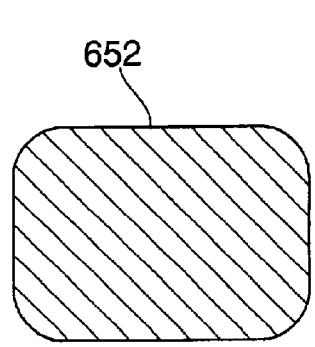

Referring to FIGS. 9A–C various embodiments of possible cross sections of various needles or prongs of the invention are illustrated. FIG. 9A illustrates a generally circular cross section 650. FIG. 9B illustrates an oval cross section 651. FIG. 9C illustrates a rectangular cross section 652 with rounded corners. The configuration of the needle or prong that pierces the stomach wall and that attaches the functional devices to the stomach wall may be selected base on desired load distribution. The needle or prong should have a relatively low profile to enable it to pierce the tissue while having enough strength to support the stimulator or adequate dimensions perpendicular to the main load directions in support of the stimulator to avoid stress concentrations and the needles or prongs tearing or cutting out of the tissue. As illustrated in FIGS. 9B and 9C, the cross section of the needle has one dimension longer than the other. This serves to increase the area over which the load is distributed or distribute the load perpendicular to the needle and the longest cross-sectional dimension.

Figure 10A:
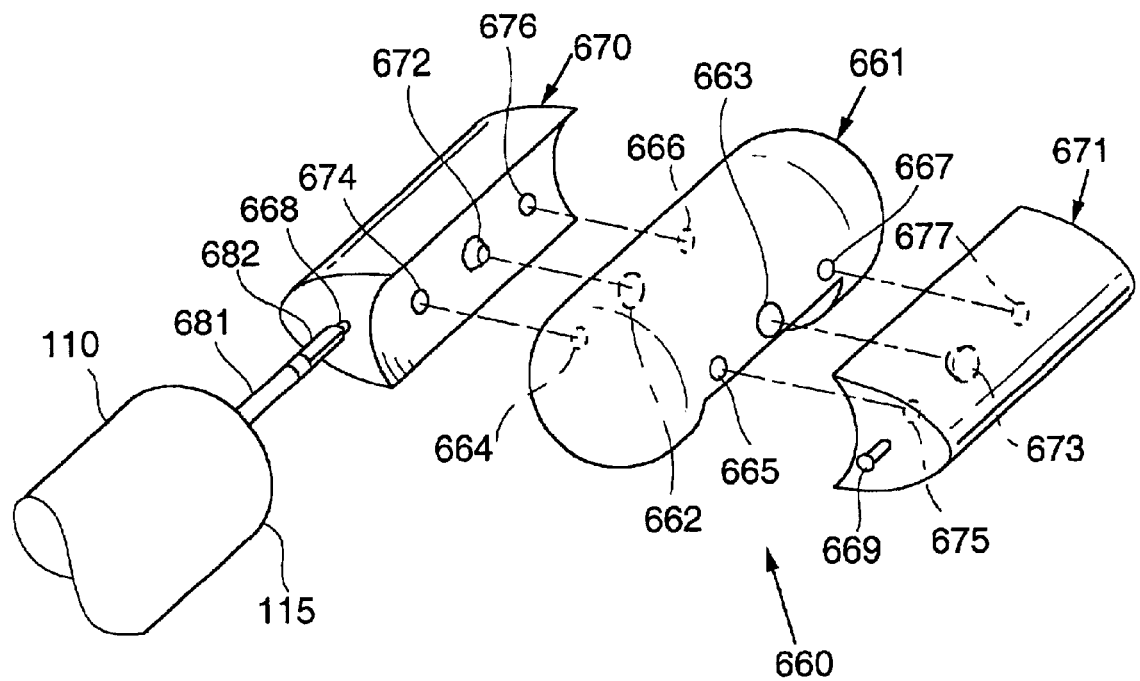
FIGS. 10A–E illustrate an alternative embodiment of the invention in which an implanted stimulator is comprised of removable replaceable modules.
Figure 10B:
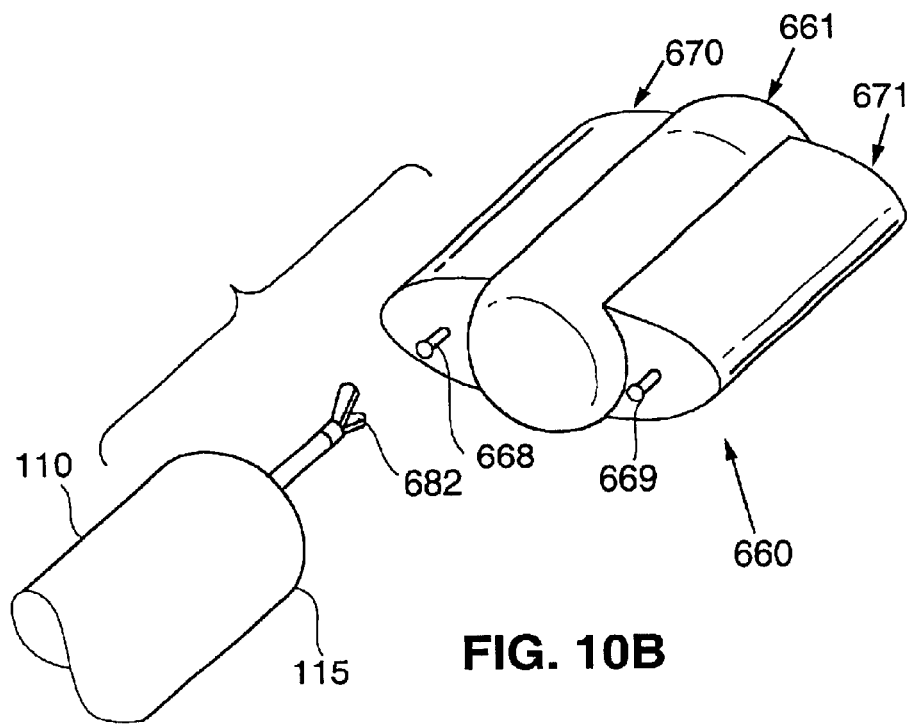

Referring to FIGS. 10A–E a device having removable replaceable modules is illustrated with instruments and a procedure for delivering and removing the modules of the device. The device 660 may take the form of any of the functional devices described herein with respect to delivery and attachment to the stomach wall. The device 660 includes a main body 661, which includes electrodes, electrical connectors, and an attachment mechanism for attaching the main body 661 to the stomach wall 104 of a patient. Attachable removable modules 670, 671 contain an electrical circuit and a battery for powering the electronic circuit to provide stimulation to the stomach wall 104. The modules 670, 671 may be used in any functional device and may also contain, for example, sensors (pH, strain gauge, glucose, pressure, temperature, impedance, EMG, EGG etc) or substance or drug delivery. As illustrated in FIG. 10A, the main body 661 of the device also includes connecting ports 662, 663 for receiving connectors 672,673 of modules 670, 671 respectively. The connectors 674, 675, 676, 676 and the connecting ports 664, 665, 666, 667 comprise magnets. The magnets may comprise, for example, neodymium iron boron magnets to lock the modules, 670, 671 onto the main body 661. When the connectors 674, 675, 676, 676 are correctly aligned and connected with the connecting ports 664, 665, 666, 667, electrical contacts 662 of the stimulator main body 661 are in electrical contact with contacts 672 of module 670, and, electrical contacts 663 of the stimulator are in electrical contact with contacts 673 of module 671. These electrical contacts 662, 663, 672, 673 each have multiple electrical contacts on them. Through contacts 672, 673 and through contacts 662, 663 a battery in a first module is coupled to the electronic circuit 25 in the other module, which delivers stimulating pulses to the stomach wall through electrodes in the stimulator, e.g. in the needle of the stimulator. As illustrated in FIG. 10A a grasping tool 681 with grasping jaws 682 on the distal end, is inserted through the endoscope 110 whereby the grasping jaws 682 grasp the knob 668 on the module 670 to manipulate the module into place on the main body 661. The module 671 similarly includes a knob 669 on its proximal end for grasping to manipulate the module 671 into place.

Figure 10C:
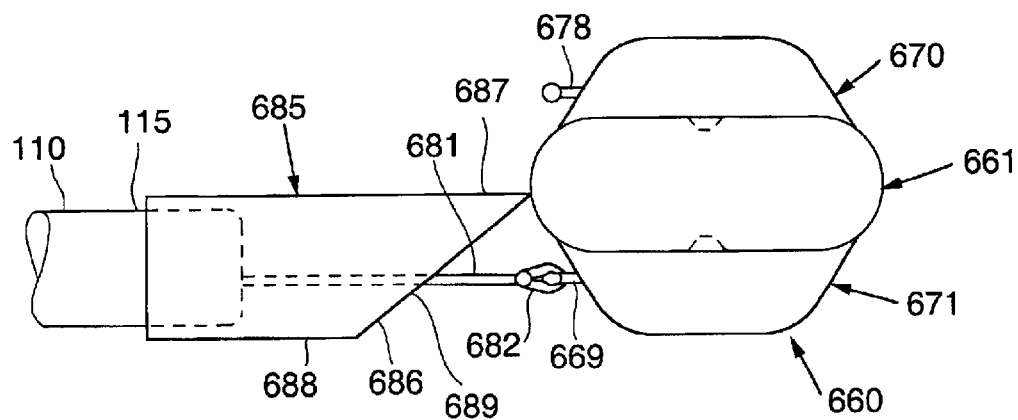
Figure 10D:
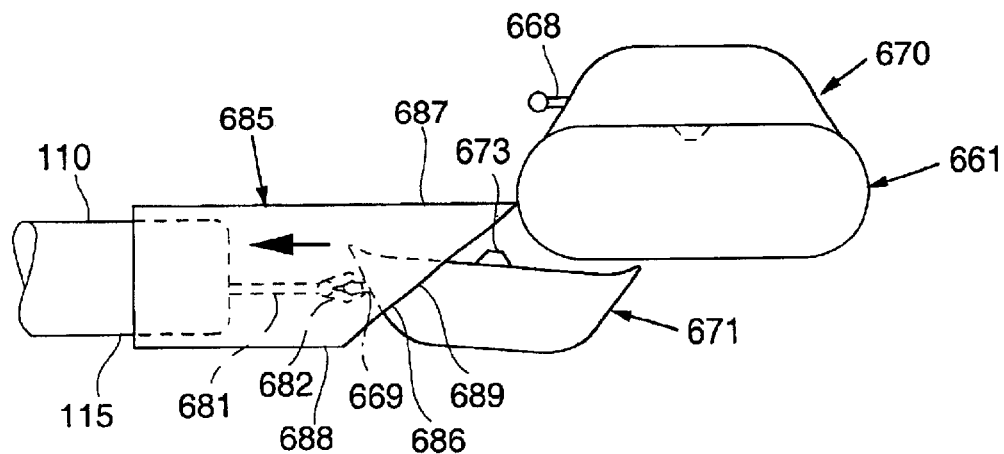
Figure 10E:
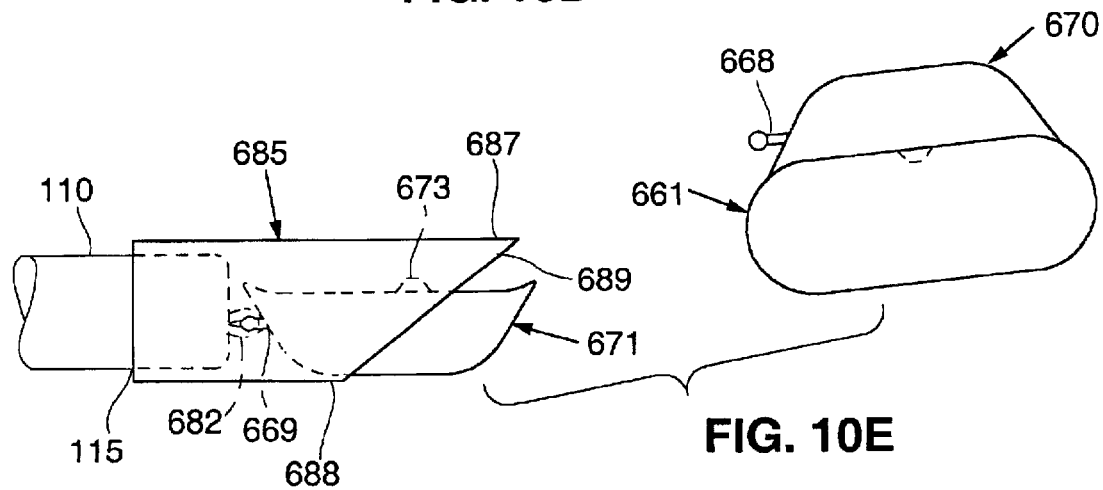

Referring to FIGS. 10C–E, an endoscope 110 and associated instruments are illustrated in the removal of a module 671 from the stimulator 660. An angulated endoscopic end cap 685 is press fit on the distal end 115 of the endoscope 110. The end cap 685 has an angled distal end 686 with a long portion 687 and a short portion 688 and an opening 689 in the distal end 686. As illustrated in FIG. 10C, the long portion 687 of the angulated cap 685 is placed against the proximal end of the device 660 to stabilize the endoscope 110 and associated instruments with respect to the device 660 and prevent relative axial movement with respect to one another. The grasping instrument 681 is used to grasp the knob 669 of the module 671. As illustrated in FIG. 10D, the grasping instrument 681 is retracted removing the module 671 from the main body 661. As further illustrated in FIG. 10E, the module 671 is further retracted through the opening 689 in the distal end 686 of the end cap 685 for removal with the endoscope 110.

Figure 11:
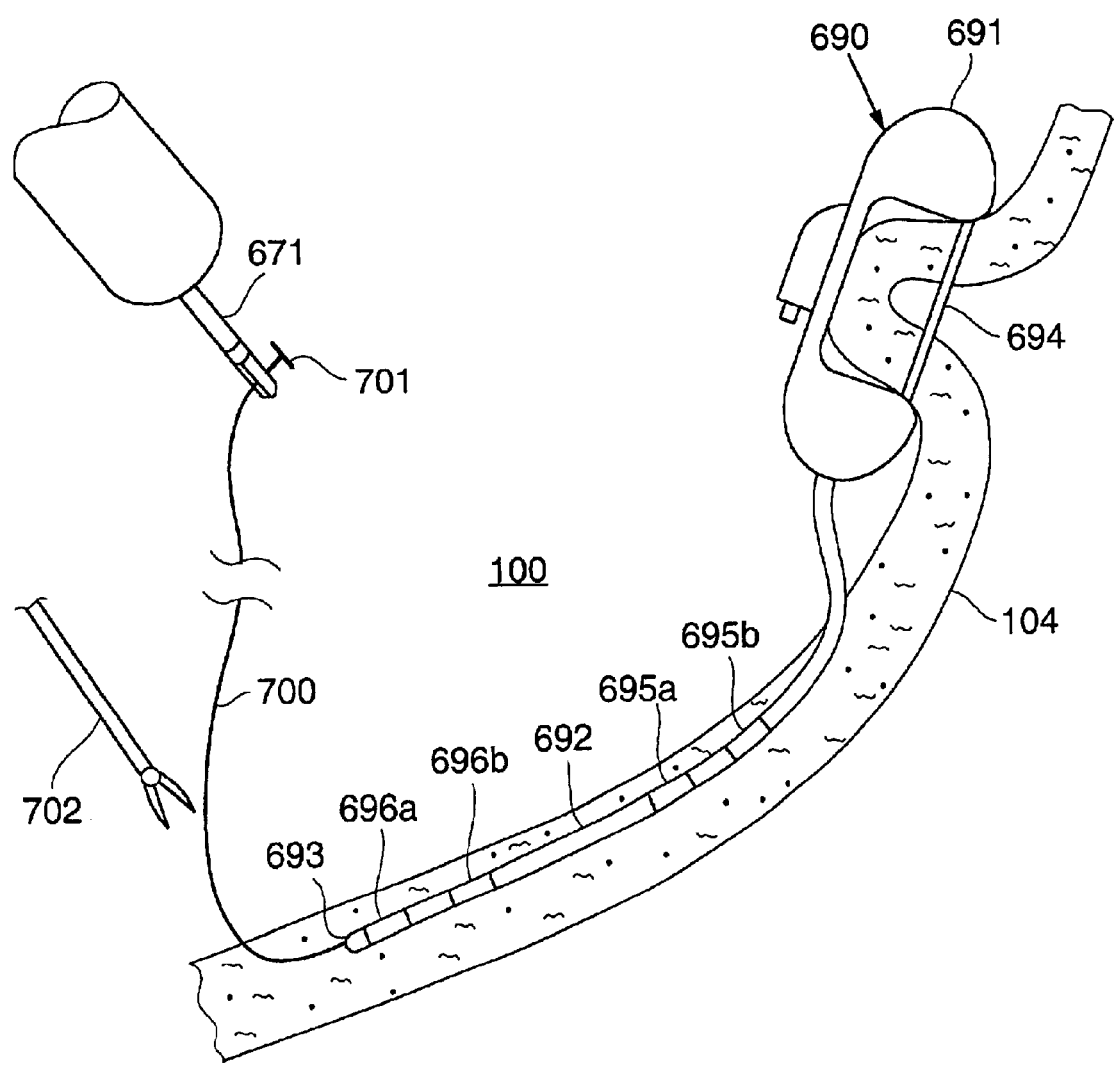
FIG. 11 illustrates a side partial cross sectional view of an alternative embodiment of a stimulator of the present invention.

Referring now to FIG. 11, another embodiment of a stimulator of the present invention is illustrated. The stimulator 690 comprises a housing 691 with a needle 694 for attaching the device to a stomach wall 104 in a manner similar to that described herein with reference to FIGS. 1, 2A–G, 3 and 4A–H. The needle 694 optionally may include electrodes. The stimulator device further comprises an elongate member 692 with bipolar ring electrode pairs 695a–b, 696a–b located at spaced locations along the elongate member 692. The electrodes 695a–b, 696a–b are coupled to electronic circuitry 25 within the housing 691 by way of connectors extending through the elongate member to the housing 691 and to the electronic circuitry 25. The electronic circuitry 25 may include various programs for stimulating the stomach wall sequentially using the electrode pairs 695a–b, 696a–b. The electrode pairs 695a–b, 696a–b may also be used to sense an electrical single in the wall of the stomach, be it inherent or from a stimulation pulse delivered by another electrode pair. The electronic circuitry 25 may be programmed to respond by delivering a stimulation signals to electrodes 695a–b, 696a–b to response to a sensed electrical signal. As such one electrode pair may be a master for a second electrode pair where the second electrode pair will be controlled to respond to the signal sent by the master. The elongate member 692 is implanted in the stomach wall after the housing 691 has been attached to the stomach wall 104. A suture 700 or wire attached to the end 693 of the elongate member 692 is placed through a portion of the stomach wall with a hollow needle so that a T-shaped end 701 extends back inside the stomach 100. The suture 700 is then pulled through the stomach wall 104 where the elongate member 692 is to be implanted, using an endoscopic grasping tool 671 that grasps the T-shaped end 701 of the suture 700, drawing the elongate member 692 into the stomach wall. The suture 700 is then cut using an endoscopic cutting instrument 702.

Figure 12A:
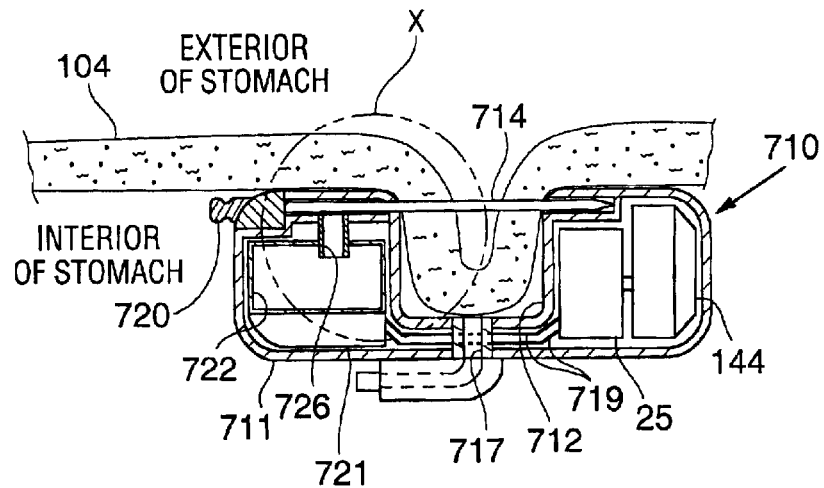
FIGS. 12A–D illustrate alternative embodiments of the functional device of the present invention in which a drug is delivered.
Figure 12D:
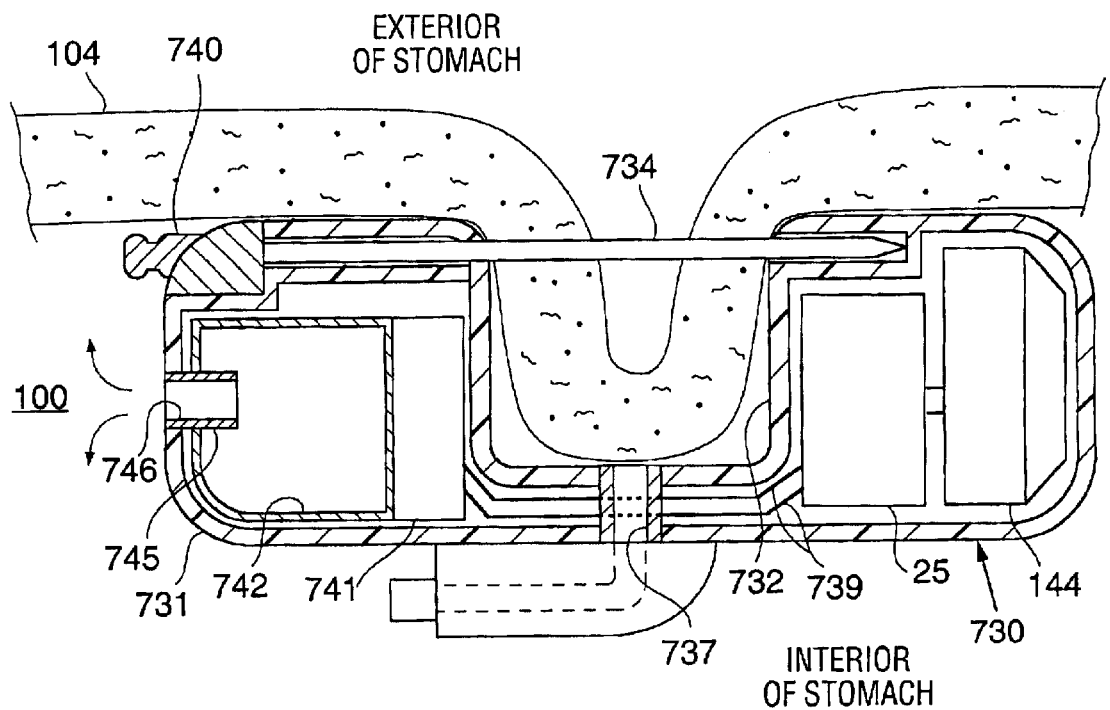
Figure 12B:
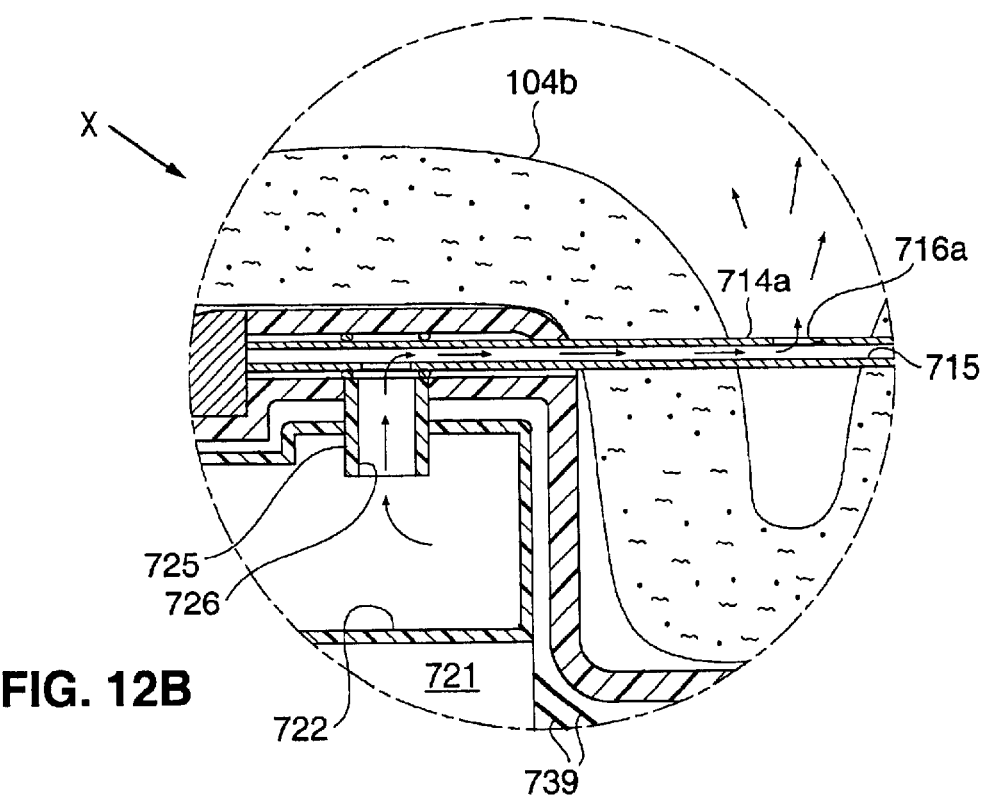
Figure 12C:
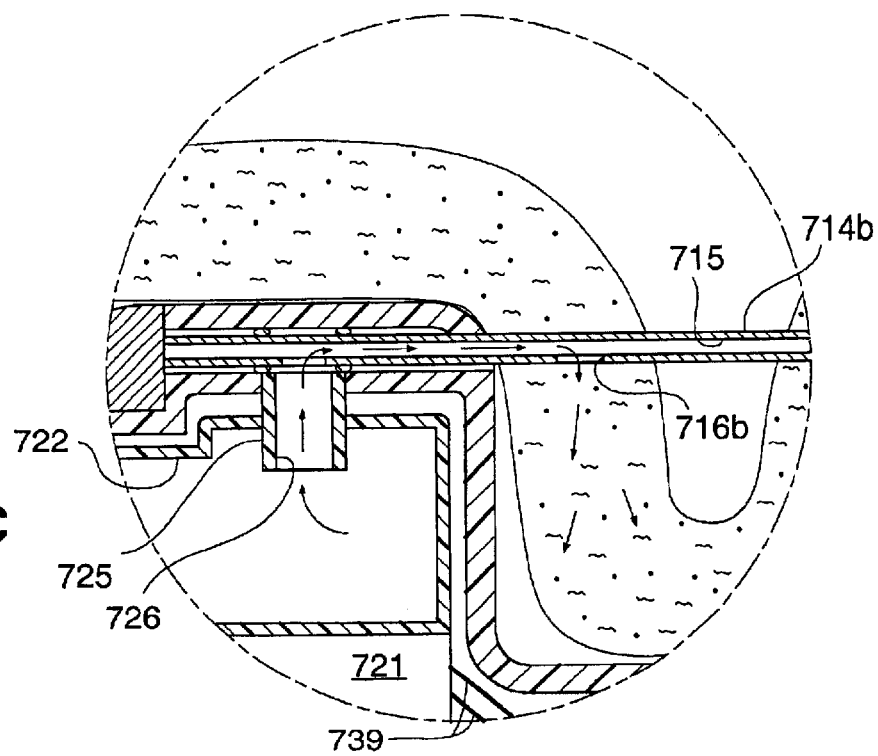

FIGS. 12A–D illustrate a functional device comprising a drug delivery mechanism. Referring to FIG. 12A, a functional device used for drug delivery is illustrated attached to a stomach wall 104. The device 710 includes a housing 711 having a chamber 712 formed therein. A vacuum pressure may be applied through opening 717 in the housing 711 to draw in a portion of the stomach wall 104. A hollow needle 714 is then advanced through the tissue of the stomach wall by advancing a knob 720 in a similar manner as described with reference to FIGS. 1 and 2A–G. The housing 711 contains a battery 144 and electronic circuitry 25. The electronic circuitry 25 is coupled to a drug reservoir and pump 721, 722 for delivering a drug through the needle 714 in one of several manners described with reference to FIGS. 12B and 12C. As illustrated in FIG. 12A–C, a tubular wall 725 provides a conduit 726 from the reservoir 721 to a lumen 715 in the needle 714. FIGS. 12B and 12C illustrate alternative embodiments of the needle 714 with different outlet ports from the needle 714. FIG. 12B illustrates a needle 714a having an outlet port 716a in the side of the needle 714a that opens the lumen 715 in the needle 714a in a direction facing the outside 104b of the stomach wall. FIG. 12C illustrates a needle 714b having an outlet port 716b in the side of the needle 714b that opens the lumen 715 in the needle 714b in a direction facing into the tissue of the stomach wall 104 engaged by the needle 714b.

In use, the electronic circuitry 25 controls the action of the pump 722 by delivering a control signal through connectors 719 coupling the electronic circuitry 25 to the drug pump 722. The electronic circuitry 25 may determine the timing and amount of drug to be delivered based on a preprogrammed regimen stored in memory in the circuitry 25. Alternatively, the programs may be altered based on sensed conditions of the stomach. To this end a sensor for sensing a parameter inside or outside the stomach, and in the stomach wall, may be provided on the functional device 710. The program may be telemetrically communicated to the electronic circuitry by way of an external controller. When a control signal is delivered to the pump, 722, the pump delivers the drug from the reservoir 721, through the conduit 726 into the lumen 715 in the needle 714 and out an outlet port 716a or 716b.

Referring to FIG. 12D, an alternative functional device used for drug delivery is illustrated attached to a stomach wall 104. The device 730 includes a housing 731 having a chamber 732 formed therein. A vacuum pressure may be applied through opening 737 in the housing 731 to draw in a portion of the stomach wall 104. A needle 734 is then advanced through the tissue of the stomach wall by advancing a knob 740 in a similar manner as described with reference to FIGS. 1 and 2A–G. The housing 731 contains a battery 144 and electronic circuitry 25. The electronic circuitry 25 is coupled to a drug reservoir and pump 741, 742 for delivering a drug from the reservoir 741, through a conduit 746 (defined by tubular wall 745), and to the inside of the stomach 100.

In use, the electronic circuitry 25 controls the action of the pump 742 by delivering a control signal through connectors 739 coupling the electronic circuitry 25 to the drug pump 742. The electronic circuitry 25 may determine the timing and amount of drug to be delivered based on a preprogrammed regimen stored in memory in the circuitry 25. Alternatively, the programs may be altered based on sensed conditions of the stomach. To this end a sensor for sensing a parameter of the stomach may be provided on the functional device 730. The program may be telemetrically communicated to the electronic circuitry by way of an external controller. When a control signal is delivered to the pump, 724, the pump delivers the drug from the reservoir 741, through the conduit 746 into the stomach 100.

Figure 13A:
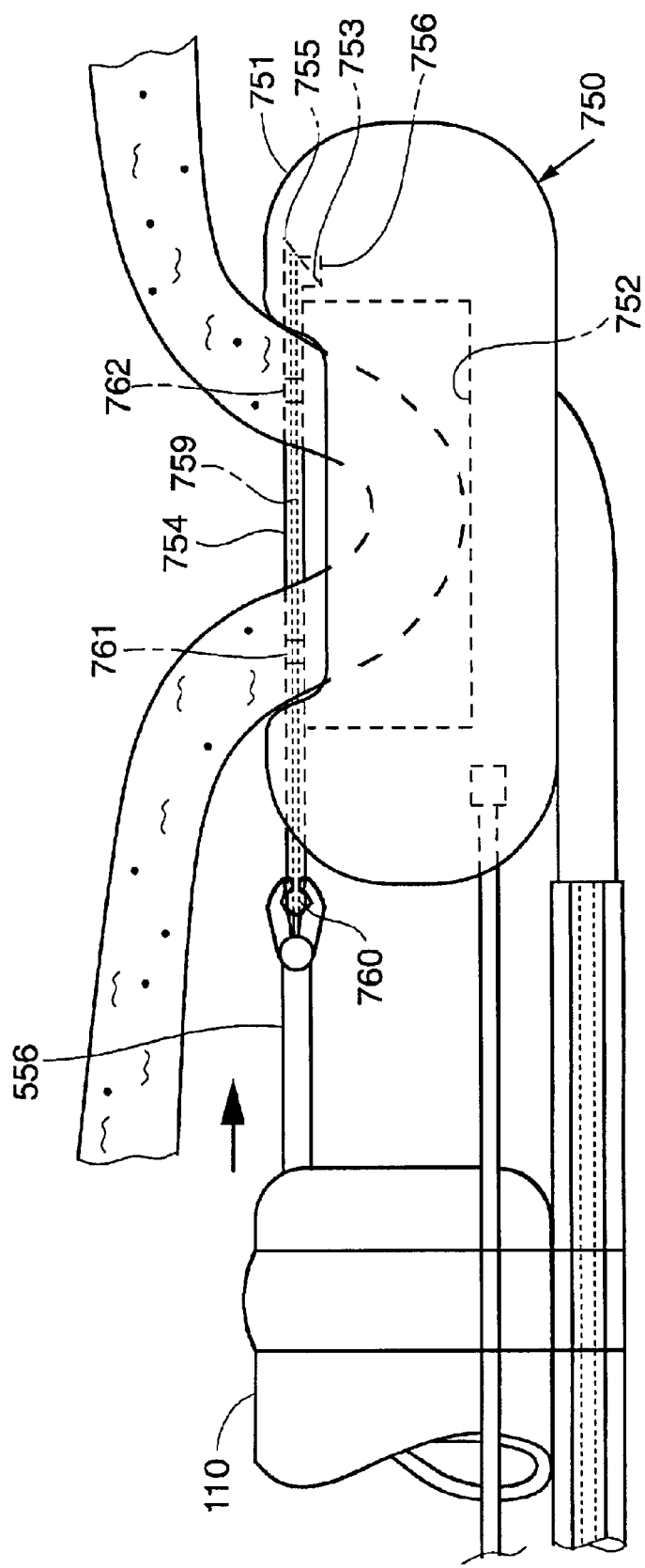
FIGS. 13A–B are side partial cross-sections of functional device with a flexible needle, and instruments for implanting the device through an endoscope.
Figure 13B:
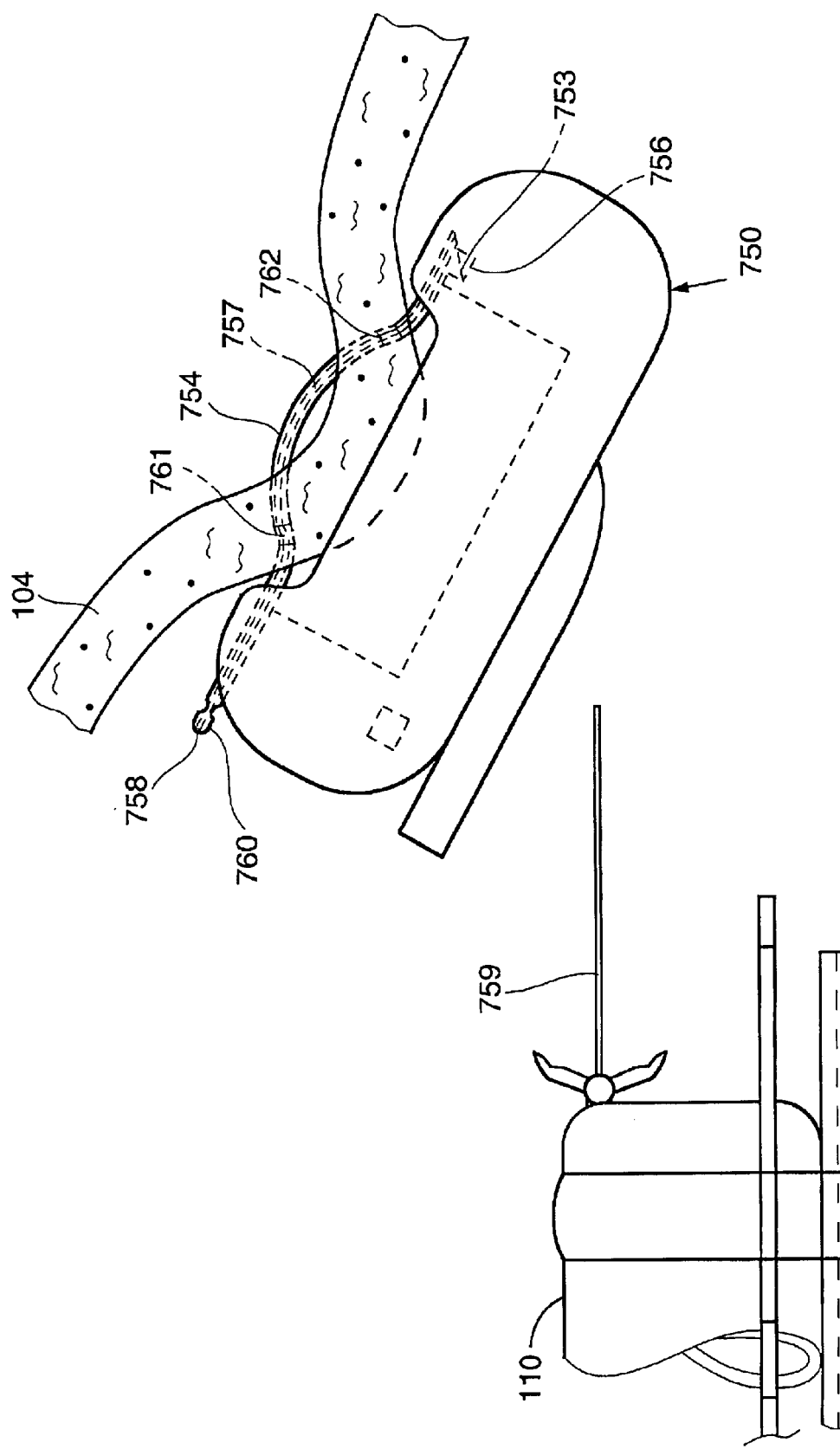

FIGS. 13A and 13B illustrate an alternative mechanism for attaching a functional device 750 to a stomach wall. The housing 751 is generally constructed in a manner similar to housing 521 of FIG. 1 and tissue is drawn into the vacuum chamber for attachment in a similar manner as described above. Additionally, the needle 754 used to attach the device 750 is constructed of a relatively flexible material so as to reduce stresses to the tissue of the stomach wall 104. The needle 754 has an additional lumen 757 to accommodate a rigid stylet 759, which allows the needle 754 to pierce through the stomach wall tissue. The distal end 755 of the needle 754 has a barb 753 to connect with the recess 756 in the housing 751 of the functional device 750 via a snap fit connection. The needle 754 may be a multi-lumen silicone tube reinforced with Nickel Titanium alloy coil. Electrodes 761, 762 for electrically stimulating the stomach wall are located in a spaced position on the needle 754 and are electrically coupled to the electronic circuit 25 in the housing 751. As illustrated in FIG. 13A, to implant the device 750, a stainless steel or titanium rod with sharp distal end is used as rigid stylet 759 to pierce the tissue of the stomach wall 104. The rigid stylet 759 is directly attached to and extends from the distal end of the grasping instrument 556, which is inserted through the endoscope 110. The stylet 759 is inserted into lumen 757 of the needle 754 through an opening 758 the knob 760 located on the outside of the housing 751. The knob 760 enables an instrument to grasp and advance or retract the needle 754 into and from the housing 751. With the stylet 759 inserted, the needle 754 is then advanced through the tissue of the stomach wall contained within the chamber 752 in the housing 751. The barb 753 at the distal end of the needle 754 catches the recess 756 within the housing 751. As illustrated in FIG. 13B, the stylet 759 is then removed leaving the needle 754 in place with the electrodes 761, 762 in electrical contact with the stomach wall for delivering stimulation pulses.

Figure 14:
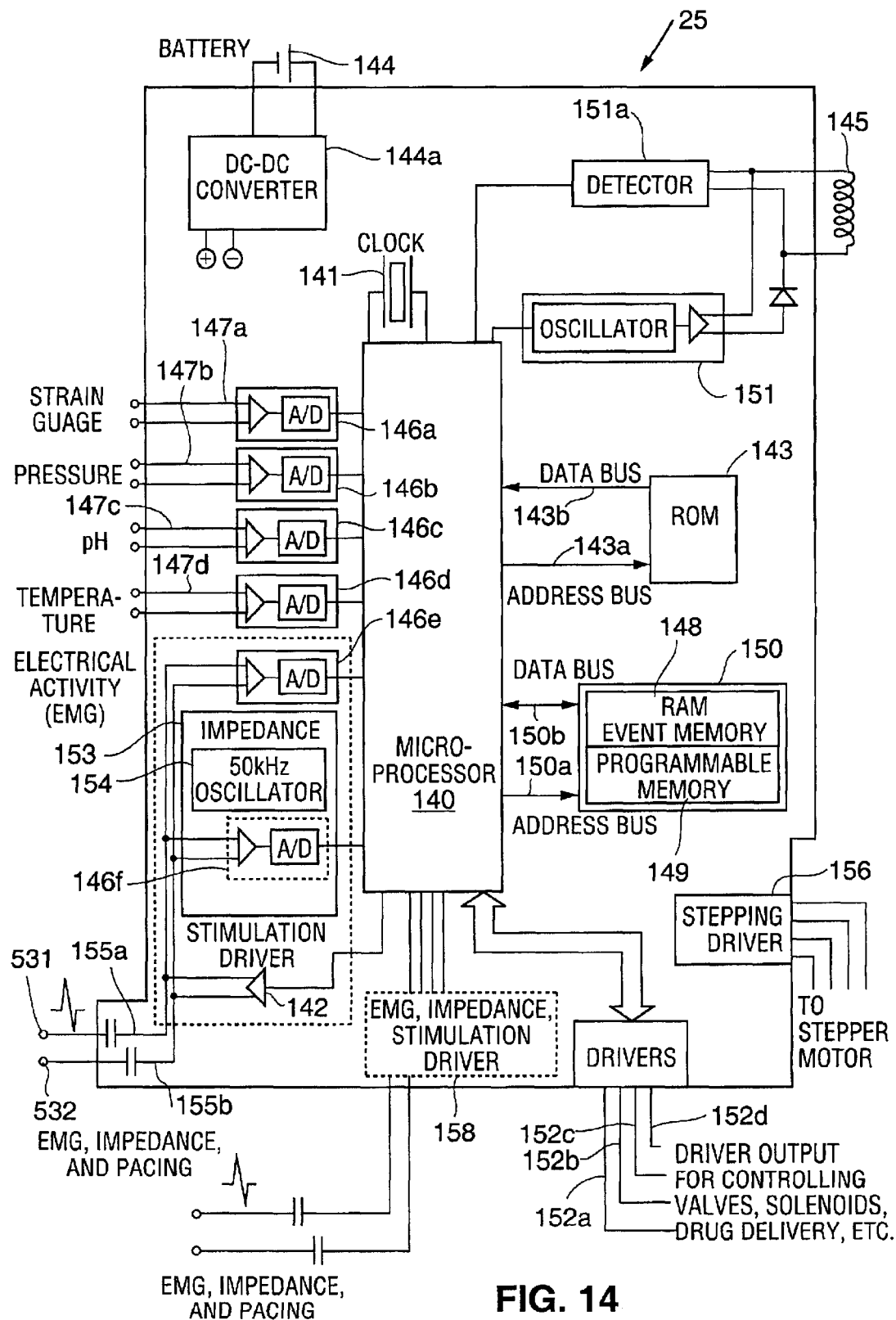
FIG. 14 is a schematic diagram of the circuit of an electronic stimulator of the present invention.

One embodiment of the electronic circuitry 25 is illustrated in FIG. 14. The electronic circuitry may be on a chip or otherwise have a standard configuration that may be used in a number of different diagnostic or therapeutic functions in various embodiments of the functional device. The electronic circuitry 25 of the stimulator is located in the housings of the various implants described herein. The circuitry 25 comprises: a microprocessor or controller 140 for controlling the operations of the electronic circuitry 25, an internal clock 141, and battery device 144 such as a pair of lithium iodine batteries for powering the various components of the circuitry 25. As such, the controller 140 and battery device 144 are coupled to each of the major components of the circuit as would be apparent to one of ordinary skill in the art. The controller 140 is coupled to stimulation driver 142, which is coupled to stimulating electrodes 531, 531 (or any of the other electrodes described herein) that are used to provide electrical stimulation in accordance with programmed parameters.

The controller 140 is coupled to ROM 143, which contains the program instructions for the controller 140 and any other permanently stored information that allows the microprocessor/controller 140 to operate. The controller 140 addresses memory in ROM 143 through address bus 143a and the ROM 143 provides the stored program instruction to the controller 140 via data bus 143b. The controller 140 controls the RF coil 145, which communicates with an external control or programming device 160 (FIG. 15), preferably via a modulated RF signal. Processor 140 is coupled to a buffered oscillator 151 that provides an RF signal to be emitted from the RF coil 145. The RF signal is preferably at about 100 kHz to 5 MHz so that the signal is efficiently transmitted through tissue. The controller 140 controls the oscillator 151 and provides data, for example, various sensed data such as pressure, pH, temperature, strain, impedance, electrical activity (EMG) etc., to be modulated with the RF signal to be delivered through the RF coil 145. When the RF coil 145 is receiving an external telemetry signal, the buffered oscillator 151 is disabled. Telemetry signals received on the RF coil 145 are detected in a detector circuit 151a and to communicated controller 140. The detector circuit 151a is preferably selected based on the modulation used for telemetry signals.

One or more sensors 147a (e.g., strain gauge), 147b (e.g., pressure), 147c (e.g., pH), 147d temperature, or electrodes 531, 532 (for sensing EMG, EGG, or impedance as well as providing stimulation), may be coupled to the controller 140 through A/D converters (with amplifiers) 146a, 146b, 146c, 146d, 146e which convert a representative analog electrical signal into a digital signal. Suitable types of these sensors are generally known in the art and may be located within, on, or external to the housing or other portions of the of the stimulator, such as the attachment mechanism or elongate member.

Controller 140 is coupled to RAM 150 via an address bus 150a for addressing a location in RAM 150 and a bi-directional data bus 150b for delivering information to and from RAM 150. The RAM 150 includes event memory 148 that temporarily stores data recorded by sensors 147a–d or electrodes 531, 532 (or other electrode pairs described herein). RAM 150 also includes a programmable memory 149 which may be programmed, for example, by an external programmer 160. The data stored in the programmable memory may include specifications for the electrical stimulation operating modes, (e.g., waveform, type of stimulations: for pacing, inducing contraction or other type) and various procedure parameters, (e.g., when to deliver a drug or electrical stimulation). Such programming may be done in response to sensed information or it may be done automatically by an external controller or as desired by a treating physician, etc. Sensed data acquired from sensors 147a–d and electrodes 531, 532 or other electrode pairs described herein, provided to the controller 140 may be stored in event memory 148 in the RAM 150. The data stored in the event memory 148, may be sent intermittently as data bursts via the RF coil 145, as opposed to continuously in order to save battery power.

The electrode 531, 532 outputs are used to provide electrical stimulation delivered through the stimulation driver 142 to the electrodes 531, 532. The stimulation modes and parameters can either be set using the external programmer 160, or they may be set in response to sensory feedback. The same electrode outputs are used to sense impedance through impedance circuit 153 and to sense electrical activity, which is delivered through A/D converter 146e. The electrodes 531, 532 are coupled through coupling capacitors 155a and 155b respectively, to the output of electrical stimulation driver 142 and the inputs of A/D converters 146e, 146f.

The impedance circuit 153 comprises a constant current source oscillator 154 that oscillates at a frequency of 50–100 kHz, and an A/D converter 146f coupled to the controller 140. The oscillator 154 provides a constant current source through electrodes 531, 532 resulting in a voltage across the electrodes 531, 532 that is representative of impedance, in view of the constant current. The voltage is provided through and is converted by A/D converter 146f to a digital signal representative of impedance. A/D converter 146f has a bandwidth that includes the 50 kHz frequency signal while filtering out the electrical stimulation signal that is delivered to the electrodes 531, 532 through electrical stimulation driver 142, and the EMG signal that is sensed by the electrodes 531, 532. Both of the outputs are filtered out by A/D converter 146f. A/D converter 146e has a bandwidth that filters out the 50–100 kHz signal. Further, when a stimulation signal is being delivered, the controller 140 does not receive signals from A/D converters 146e and 146f. Thus the EMG and impedance sensing functions and the stimulation delivery functions are separated through the electronic circuitry 25, though using the same electrodes.

An additional circuit 158 (or a plurality of such circuits) may be provided in the electronic circuitry 25 that are comprised of the same components and are configured as A/D converter 146e, impedance circuit 153 and stimulation driver 142. Such circuit may provide stimulation, impedance, EMG or EGG sensing for an additional pair of electrodes.

The battery 144 has its output supplied to a DC-to-DC converter 144a to provide a higher voltage, which is utilized for electrical stimulation pulses. The DC-to-DC converter 144a is conventional and provides an output voltage of 15 to 20 volts. Further, the circuitry 25 may include one or more drivers 152a, 152b, 152c, 152d that drive various devices such as, for example, diagnostic or therapeutic electromechanical devices such as controlling valves, solenoids, etc. for drug deliver, etc. The controller 140 provides a signal to a driver 152a–d based on a preset program in ROM 143 and/or on sensed parameters stored in RAM 150. The circuit may also include a stepping driver 156 coupled to a stepper motor, for example, a precise drug delivery mechanism.

Figure 15:
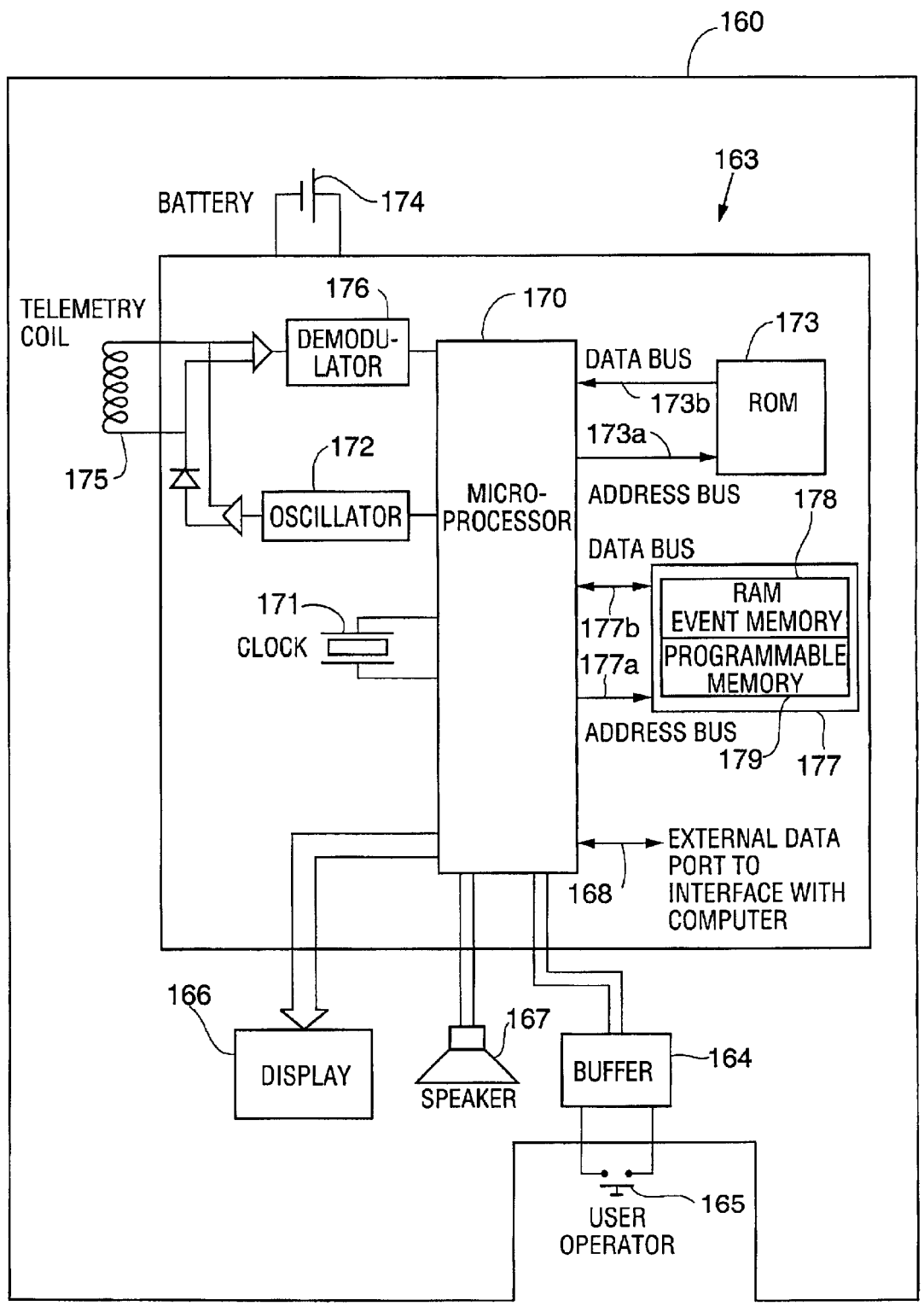
FIG. 15 is a schematic diagram of the circuit of a programmer/recorder of the present invention.

FIG. 15 illustrates the electronic circuitry 163 for external programmer 160. The electronic circuitry 163 comprises: a microprocessor or controller 170 for controlling the operations of the electronic circuitry, an internal clock 171, and a power source 174 such as a battery device for powering the various components of the circuit 163. As such, the controller 170 and battery device 174 are coupled to each of the major components of the circuit as would be apparent to one of ordinary skill in the art. The controller 170 is coupled to a speaker 167 for that provides audible alerts and a display 166 such as a CRT to display data such as recorded data, sensed parameters, treatment parameters and status of the device (e.g. position or battery charge status). The controller 170 is coupled through a buffer 164 to external input device 165 that is used to provide program parameter input, e.g. from a user, for a user to request data displayed in a desired format through display 166 or speaker 167, or to turn the device on and off. The external programmer 160 is also provided with an external data port 168 to interface with a computer and provide a means for bi-directional communication of data or commands. The computer may provide programming or data to the controller/microprocessor 170. A user may also interface with the computer to provide treatment protocols or changes in protocols, etc. Also, a user may control the turning on and off of the stimulation program.

The controller 170 is coupled to ROM 173, which contains the program instructions for the controller 170 and any other permanently stored information that allows the microprocessor/controller to operate. The controller 170 addresses memory in ROM 173 through address bus 173a and the ROM 173 provides the stored program instructions to the controller 170 via data bus 173b. The controller 170 controls the RF coil 175, which communicates with stimulator electronic circuitry 25 (FIG. 13) through its RF coil 145. Processor 170 is coupled to an oscillator 172 that provides an RF signal, preferably having a characteristic frequency of 500 kHz or higher, to be emitted from the RF coil 175. The controller 170 controls the oscillator 172 and provides data to be modulated with the RF signal, for example, programming information, stimulation parameters, etc. The RF coil 175 also receives information transmitted via RF signal from RF coil 145 on the stimulator electronic circuitry 25 such as various sensed data, e.g., pressure, pH, impedance, electrical activity (EMG) etc. The received RF signal is passed through demodulator 176 and is transmitted to the controller 170. The data is delivered to the event memory 178 in RAM 177 by way of data bus 177b for temporary storage. The data may be retrieved from RAM 177 by addressing the storage location via the address bus 177a.

Event memory 178 temporarily stores data recorded by sensors 147a–147 and electrodes 531, 532 and delivered via telemetry to the external programmer 160, until the data is downloaded onto a computer using the external data port 168. The RAM 177 also includes a programmable memory 179 which may be programmed, for example, to specify operating modes such as waveform, frequency, etc. which programming is then telemetrically communicated to the stimulator electronic circuitry 25. The modes and parameters can either be set using an external programmer 160 or set in response to sensory feedback.

In an alternative embodiment, the device includes a housing, electrodes and minimal electronics and an electromagnetic coil. This device is powered by an external electromagnetic coil, which is placed on the patient's abdomen near the implanted device. The electrical stimulation parameters are controlled real-time by an external unit.

Figure 16A:
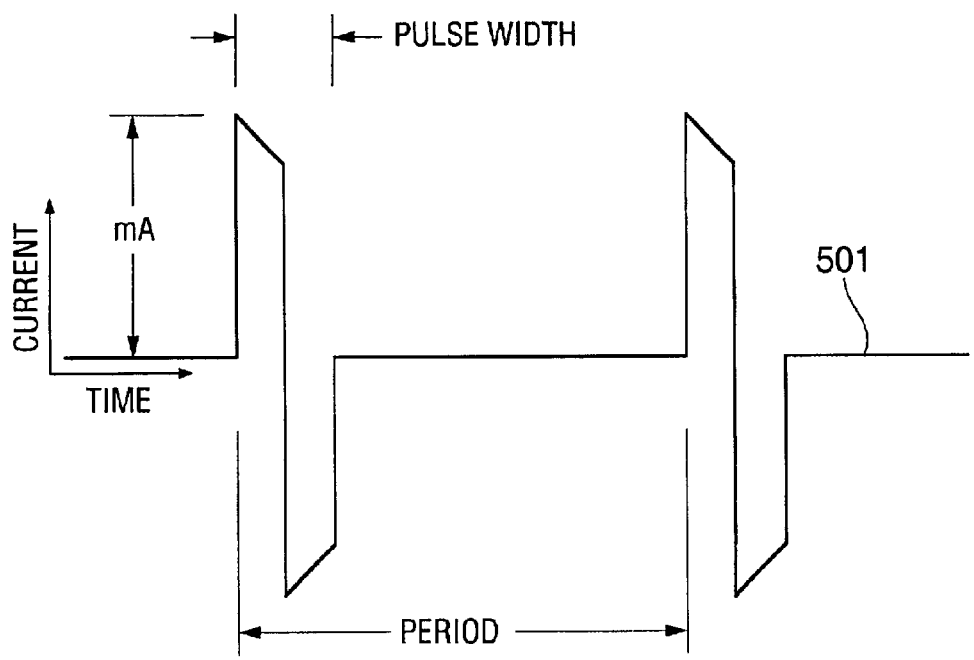
FIGS. 16A and 16B illustrate exemplary stimulation waveforms.
Figure 16B:
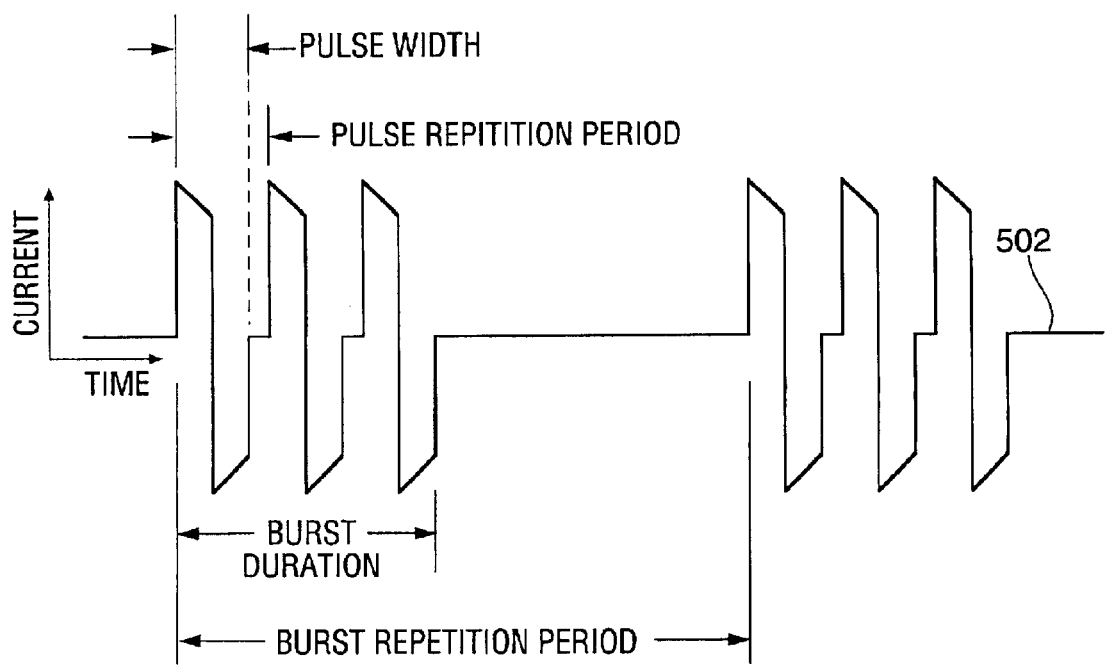

The electronic circuitry 25 is capable of producing various types of programmable waveforms. FIGS. 16A and 16B illustrate examples of stimulation waveforms that may be used in stimulating the smooth muscle layer of the stomach wall. FIG. 16A illustrates a waveform design for stimulating the stomach wall at a pacing rate. In one embodiment, the waveform 501 has a pulse amplitude of 1 to 30 mA, a pulse width of between 0.1 and 500 ms, and a frequency of about between 2 to 12 cycles per minute (this corresponds to a repetition period of between 5 to 30 seconds). FIG. 16B illustrates an alternative waveform design for stimulating the stomach wall. The waveform 502 utilizes bursts of pulses rather than a single pulse. The burst repetition rate is selected, preferably, to be between about 2 to 12 cycles per minute (this corresponds to a burst repetition period of between 5 to 30 seconds). The duration of a pulse in this example is between about 100 µs and 20 ms, and has an amplitude of about 1–30 mA. The frequency of the burst pulses during a burst period is about 50 Hz to 10 KHz corresponding to a pulse repetition period of 100 µs to 20 ms. The burst duration can vary from about 0.1 ms to 1 second. As is well known to those skilled in the art, there are many different types of electrical stimulation programs and strategies which can be utilized for providing electrical stimulation parameters through the circuitry 25, the principal focus being providing electrically stimulating parameters for the stomach. Stimulation may also be done utilizing phasic, unipolar or asymmetric stimulation waveforms.

The invention has been described with reference to preferred embodiments and in particular to a gastric stimulator, the present invention contemplates that the attachment devices may be used to attach a number of functional devices to the wall of the stomach for sensing parameters of the stomach or its environment, or for diagnosing or providing treatment to the stomach. The attachment device may incorporate such sensing, diagnostic or treatment devices within the attachment device. Such functional devices may also be separately attached to the stomach and/or to the attachment device or to another functional device. The attachment device or functional devices may communicate to an external recorder or controller by way of telemetry. They may be battery powered or powered by inductive coupling. A plurality of functional devices may be attached to the stomach wall. The functional devices may be programmed to respond to information or signals delivered by other functional devices whether the signals are delivered from one device to another through conductors or whether the signals are delivered, e.g. through the stomach wall or medium within the stomach.

While the invention has been described with reference to particular embodiments, it will be understood to one skilled in the art that variations and modifications may be made in form and detail without departing from the spirit and scope of the claimed invention. Such modifications may include substituting other elements, components or structures which perform substantially the same function in substantially the same way to achieve substantially the same result that the invention can be practiced with modification within the scope of the following claims.

What is claimed is:

1. A device for attaching to a stomach wall to treat or diagnose a patient, said device comprising:
   a housing comprising:
      a chamber configured to receive tissue of a stomach wall; and
      a port in fluid communication with the chamber and including a connection portion configured to couple the port with a vacuum source to draw the tissue into the chamber;
   an attachment mechanism configured to attach the housing to the stomach wall, wherein the connection portion is configured to be detached from the vacuum source leaving the attachment mechanism attaching the housing to the stomach wall; and
   a functional portion coupled to the housing;
   the attachment mechanism comprising a piercing device, wherein the piercing device comprises a stiff portion and a flexible portion wherein the piercing portion is sufficiently stiff to pierce through the tissue with the flexible portion and wherein the piercing portion is removable from the pierced tissue while leaving the flexible portion in place.

2. The device of claim 1 further comprising
   electronic circuitry contained within the housing; and
   at least one stimulating electrode coupled to the housing and electrically coupled to the electronic circuitry, and wherein said electronic circuitry is configured to deliver electrically stimulating signals to the stomach through the at least one stimulating electrode.

3. The device of claim 2 wherein the at least one stimulating electrode is located on the piercing mechanism.

4. A device for attaching to a stomach wall to treat or diagnose a patient, said device comprising:
- a housing comprising:
  - a chamber configured to receive tissue of a stomach wall; and
  - a port in fluid communication with the chamber and including a connection portion configured to couple the port with a vacuum source to draw the tissue into the chamber;
- an attachment mechanism configured to attach the housing to the stomach wall, wherein the connection port is configured to be detached from the vacuum source leaving the attachment mechanism attaching the housing to the stomach wall;
- electronic circuitry contained within the housing; and
- at least one stimulating electrode coupled to the housing and electrically coupled to the electronic circuitry, and wherein said electronic circuitry is configured to deliver electrically stimulating signals to the stomach through the at least one stimulating electrode.

5. The device of claim 4 wherein the attachment mechanism comprises a piercing device configured to pierce the tissue of the stomach wall drawn into the chamber and wherein the at least one stimulating electrode is located on the piercing mechanism.

6. A method for treating or diagnosing a patient comprising the steps of:
- providing a functional device to be attached to a stomach wall of the patient, the functional device comprising:
  - a housing comprising:
    - a chamber configured to receive tissue of a stomach wall; and
    - a port in fluid communication with the chamber and including a connection portion configured to couple the port with a vacuum source;
  - an attachment mechanism configured to attach the housing to the stomach wall; and
  - a functional portion coupled to the housing;
- locating the chamber adjacent a portion of a stomach wall;
- applying a vacuum to the chamber to draw the portion of the stomach wall into the chamber; and
- attaching the housing to the portion of the stomach wall drawn into the chamber;
- providing at least one stimulating electrode coupled to the housing and electronic circuitry electrically coupled to the at least one stimulating electrode; and
- delivering electrically stimulating signals to the stomach wall from the electronic circuitry through the at least one stimulating electrode.

* * * * *